United States Patent
Fowler et al.

(10) Patent No.: US 9,145,548 B2
(45) Date of Patent: Sep. 29, 2015

(54) FOOT AND MOUTH DISEASE VIRUS WITH INCREASED STABILITY AND ITS USE AS VACCINE

(75) Inventors: Veronica Fowler, Alton (GB); Nick Knowles, Aldershot (GB); Paul Barnett, Windlesham (GB)

(73) Assignee: THE PIRBRIGHT INSTITUTE, Pirbright (GB)

( * ) Notice: Subject to any disclaimer, the term of this patent is extended or adjusted under 35 U.S.C. 154(b) by 112 days.

(21) Appl. No.: 13/821,191

(22) PCT Filed: Sep. 8, 2011

(86) PCT No.: PCT/GB2011/051678
§ 371 (c)(1),
(2), (4) Date: May 17, 2013

(87) PCT Pub. No.: WO2012/032348
PCT Pub. Date: Mar. 15, 2012

(65) Prior Publication Data
US 2013/0230549 A1    Sep. 5, 2013

(30) Foreign Application Priority Data
Sep. 8, 2010 (GB) .................... 1014965.6

(51) Int. Cl.
*C12N 7/00* (2006.01)
*A61K 39/135* (2006.01)
*C07K 14/005* (2006.01)

(52) U.S. Cl.
CPC ............. *C12N 7/00* (2013.01); *A61K 39/135* (2013.01); *C07K 14/005* (2013.01); *C12N 2770/32122* (2013.01); *C12N 2770/32134* (2013.01)

(58) Field of Classification Search
None
See application file for complete search history.

(56) References Cited

U.S. PATENT DOCUMENTS

2004/0001864 A1    1/2004    King et al.

FOREIGN PATENT DOCUMENTS

EP    0048455 A2    3/1982

OTHER PUBLICATIONS

Jangra et al. (Virus Research. 2005; 112:52-59).*
Twomey et al. (Virology. 1995; 206:69-75).*
Van Vlijmen et al. Journal of Molecular Biology. 1998; 275:295-308).*
Anil et al. (Biologicals. 2012; 40:426-430).*
Acharya et al., The three-dimensional structure of foot-and-mouth disease virus at 2.9 A resolution, *Nature*, 337:709-16 (1989).
Alexandersen et al., The pathogenesis and diagnosis of foot-and-mouth disease, *J. Comp. Path.* 129:1-36 (2003).
Baranoski et al., Cell recognition by foot-and-mouth disease virus that lacks the RGD integrin-binding motif: flexibility in aphthovirus receptor usage, *J. Virology*, 74:1641-7 (2000).
Baxt et al., The adsorption and degradation of foot-and-mouth disease virus by isolated BHK-21 cell plasma membranes, *Virology*, 116:391-405 (1982).
Cao et al., Synthesis of foot-and-mouth disease virus empty capsids in insect cells through acid-resistant modification, Scientia Agricultura Sinica, (2009).
Donaldson et al., Predicting the spread of foot and mouth disease by airborne virus, *Rev. Sci. Tech. Office*, 21:569-75 (2002).
Fowler et al., Marker vaccine potential of a foot-and-mouth disease virus with a partial VP1 G-H loop deletion, *Elsevier*, 28:3428-34.
Fry et al., The structure of foot-and-mouth disease virus, *Curr. Top. Microbiol. Immunol.* 288:71-101 (2005).
Knowles et al., Outbreak of foot-and-mouth disease virus serotype O in the UK caused by a pandemic strain, *Vet. Rec.* 148:258-9 (2001).
Mateo et al., Complete alanine scanning of intersubunit interfaces in a foot-and-mouth-disease virus capsid revleas critical contributions of many side chains to particle stability and viral function, *J. Biol. Chem.* 278:41019-27 (2003).
Mateo et al., Engineering viable foot-and-mouth disease viruses with increased thermostability as a step in the development of improved vaccines, *J. Virology*, 82:12232-40.
Mateo et al., Thermostable variants are not generally represented in foot-and-mouth disease virus quasispecies, *J. Virol.* 88(3):859-64 (2007).
Rweyemamu et al., Foot-and-mouth disease and international development, *Adv. Vir. Res.* 53:111-26 (1999).
Tosh et al., Nucleotide sequence of the structural protein-encoding region of foot-and-mouth disease virus A22-India, 20:269-75 (2000).
International Search Report and Written Opinion of the international searching authority, European Patent Office, PCT/GB2011/051678, dated Dec. 13, 2011.
International Preliminary Report on Patentability issued in connection with PCT/GB2011/051678, dated Mar. 12, 2013.

* cited by examiner

*Primary Examiner* — Shanon A Foley
(74) *Attorney, Agent, or Firm* — Marshall, Gerstein & Borun LLP

(57) ABSTRACT

The present invention provides a foot and mouth disease (FMD) virus having improved stability compared to the field isolate of the same subtype, wherein the virus comprises one or more amino acid mutations along a line of symmetry of the capsid structure. The present invention also relates to a vaccine comprising such an FMD virus and its use to prevent foot and mouth disease.

7 Claims, 10 Drawing Sheets

| Virus | Log titre at 4°C 1hr | Log titre at 50°C 1hr | Log titre at 55°C 1hr | Log titre at 60°C 1hr |
|---|---|---|---|---|
| Field Isolate | $10^{4.8}$ tcid50/ml | Inactivated | inactivated | Inactivated |
| A+ | $10^{5.9}$ tcid50/ml | $10^{4.8}$ tcid50/ml | $10^{0.2}$ tcid50/ml | Inactivated |

| Virus | Log reduction at 50°C 1hr | Log reduction at 55°C 1hr | Log reduction at 60°C 1 hr |
|---|---|---|---|
| Field Isolate | 4.8 | 4.8 | 4.8 |
| A+ | 1.1 | 5.7 | 5.9 |
| A- | 1.2 | 5.4 | 5.7 |

FIG. 5

```
               10        20        30        40        50        60        70        80
           ....|....|....|....|....|....|....|....|....|....|....|....|....|....|....|....|
           < VP4
A/IRN/2/87 GAGQSSPATGSQNQSGNTGSIINNYYMQQYQNSMDTQLGDNAISGGSNEGSTDTTSTHTNNTQNNDWFSKLASSAFTGLF
mutant strn ................................................................................

90       100       110       120       130       140       150       160
           ....|....|....|....|....|....|....|....|....|....|....|....|....|....|....|....|
           VP4 >< VP2
A/IRN/2/87 GALLADKKTEETTLLEDRILTTRNGHTTSTTQSSVGVTYGYSTGEDHVSGPNTSGLETRVVQAERFFKKHLFDWTPDKPF
mutant strn ................................................................................

170       180       190       200       210       220       230       240
           ....|....|....|....|....|....|....|....|....|....|....|....|....|....|....|....|
A/IRN/2/87 GHLEKLELPTEHTGVYGHLVESFAYMRNGWDVEVSAVGNQFNGGCLLVAMVPEWKEFTQREKYQLTLFPHQFISPRTNMT
mutant strn ..SAR........A..................T....................K.........................

250       260       270       280       290       300       310       320
           ....|....|....|....|....|....|....|....|....|....|....|....|....|....|....|....|
                                                              VP2 >< VP3
A/IRN/2/87 AHITVPYLGVNRYDQYKKHKPWTLVVMVVSPLTTSSIAAGQIKVYANIAPTHVHVAGELPSKEGIVPVACSDGYGGLVTT
mutant strn ....................................S...........................................

330       340       350       360       370       380       390       400
           ....|....|....|....|....|....|....|....|....|....|....|....|....|....|....|....|
A/IRN/2/87 DPKTADPVYGMVYNPPRTNYPGRFTNLLDVAEACPTLLCFENGKPYVETRTDDQRLLAKFDVSLAAKHMSNTYLAGIAQY
mutant strn .............................................................P..................

410       420       430       440       450       460       470       480
           ....|....|....|....|....|....|....|....|....|....|....|....|....|....|....|....|
A/IRN/2/87 YAQYSGTINLHFMFTGSTDSKARYMVAYVPPGVDTPPDAPERAAHCIHAEWDTGLNSKFTFSIPYMSAADYAYTASDVAE
mutant strn ................................................................................

490       500       510       520       530       540       550       560
           ....|....|....|....|....|....|....|....|....|....|....|....|....|....|....|....|
                                                        VP3 >< VP1
A/IRN/2/87 TTNVQGWVCIYQITHGKAEQDTLVVSVSAGKDFELRLPIDPRAQTTATGESADPVTTTVENYGGETQVRRRQHTDVSFIM
mutant strn ....................A............................................................

570       580       590       600       610       620       630       640
           ....|....|....|....|....|....|....|....|....|....|....|....|....|....|....|....|
A/IRN/2/87 DRFVKINPVTPTHVIDLMQTHQHALVGALLRAATYYFSDLEIVVRHEGNLTWVPNGAPEAALSNTSNPTAYHKEPFTRLA
mutant strn ................................................................................

650       660       670       680       690       700       710       720
           ....|....|....|....|....|....|....|....|....|....|....|....|....|....|....|....|
A/IRN/2/87 LPYTAPHRVLATVYNGTNKYAATGARRGDLGSLAARVAAQLPSSFNFGAIRATTIHELLVRMRRAELYCPRPLLAMEVSA
mutant strn .........................DS.....P................................................

730
           ....|....|....|.
           VP1 >< 2A
A/IRN/2/87 EGRHKQKIIAPAKQLL
mutant strn ................
```

FIG. 6

```
                                       10        20        30        40        50        60        70
                                ....|....|....|....|....|....|....|....|....|....|....|....|....|....|
                                < VP4
A/IRN/2/87 fs                   GAGQSSPATGSQNQSGNTGSIINNYYMQQYQNSMDTQLGDNAISGGSNEGSTDTTSTHTNNTQNNDWFSK
mutant strn                     GAGQSSPATGSQNQSGNTGSIINNYYMQQYQNSMDTQLGDNAISGGSNEGSTDTTSTHTNNTQNNDWFSK
O1/BFS1860/UK/67 (AY593816)     GAGQSSPATGSQNQSGNTGSIINNYYMQQYQNSMDTQLGDNAISGGSNEGSTDTTSTHTNNTQNNDWFSK
C3/Resende/BRA/55 (AY593807)    GAGQSSPATGSQNQSGNTGSIINNYYMQQYQNSMDTQLGDNAISGGSNEGSTDTTSTHTTNTQNNDWFSK
Asia1/PAK/1/54 (AY593795)       GAGQSSPATGSQNQSGNTGSIINNYYMQQYQNSMDTQLGDNAISGGSNEGSTDTTSTHTTNTQNNDWFSR
SAT1/BOT/1/68 (AY593845)        GAGQSSPATGSQNQSGNTGSIINNYYMQQYQNSMDTQLGDNAISGGSNEGSTDTTSTHTNNTQNNDWFSK
SAT2/ZIM/7/83 (AF136607)        GAGHSSPVTGSQNQSGNTGSIINNYYMQQYQNSMDTQLGDNAISGGSNEGSTDTTSTHTNNTQNNDWFSK
SAT3/BEC/1/65 (AY593853)        GAGQSSPATGSQNQSGNTGSIINNYYMQQYQNSMDTQLGDNAISGGSNEGSTDTTSTHTNNTQNNDWFSK 80        90       100       110       120       130       140
                                ....|....|....|....|....|....|....|....|....|....|....|....|....|....|
                                          VP4 >< VP2
A/IRN/2/87 fs                   LASSAFTGLFGALLADKKTEETTLLEDRILTTRNGHTTSTTQSSVGVTYGYSTGEDHVSGPNTSGLETRV
mutant strn                     LASSAFTGLFGALLADKKTEETTLLEDRILTTRNGHTTSTTQSSVGVTYGYSTGEDHVSGPNTSGLETRV
O1/BFS1860/UK/67 (AY593816)     LASSAFSGLFGALLADKKTEETTLLEDRILTTRNGHTTSTTQSSVGVTYGYATAEDFVSGPNTSGLETRV
C3/Resende/BRA/55 (AY593807)    LASSAFSGLFGALLADKKTEETTLLEDRILTTRNGHTTSTTQSSVGVTYGYATAEDSSSGPNTSGLETRV
Asia1/PAK/1/54 (AY593795)       LASSAFSGLFGALLADKKTEETTLLEDRILTTRNGHTTSTTQSSVGVTYGYAVTEDAVSGPNTSGLETRV
SAT1/BOT/1/68 (AY593845)        LAQSAFSGLVGALLADKKTEETTLLEDRILTTRNGHTTSTTQSSVGVTYGYALTDKFLPGPNTNGLETRV
SAT2/ZIM/7/83 (AF136607)        LAQSAISGLFGALLADKKTEETTLLEDRIVTTRHGTTTSTTQSSVGITYGYADADSFRPGPNTSGLETRV
SAT3/BEC/1/65 (AY593853)        LAQSAISGLFGALLADKKTEETTHLEDRILTTRHNTTTSTTQSSVGVTYGYASADRFLPGPNTSGLESRV 150       160       170       180       190       200       210
                                ....|....|....|....|....|....|....|....|....|....|....|....|....|....|
                                                                     VP2-88             VP2-110
A/IRN/2/87 fs                   VQAERFFKKHLFDWTPDKPFGHLEKLELPTEHTGVYGHLVESFAYMRNGWDVEVSAVGNQFNGGCLLVAM
mutant strn                     VQAERFFKKHLFDWTPDKPFGHSARLELPTEHAGVYGHLVESFAYMRNGWDVEVTAVGNQFNGGCLLVAM
O1/BFS1860/UK/67 (AY593816)     VQAERFFKTHLFDWVTSDSFGRYHLLELPTDHKGVYGSLTDSYAYMRNGWDVEVTAVGNQFNGGCLLVAM
C3/Resende/BRA/55 (AY593807)    HQAERFFKMTLFDWVPSQNFGHMHKVVLPTDPKGVYGGLVKSYAYMRNGWDVEVTAVGNQFNGGCLLVAL
Asia1/PAK/1/54 (AY593795)       TQAERFFKTHLFDWTPNLAFGHCHFKYGSLMDSYAYMRNGWDIEVTAVGNQFNGGCLLVAL
SAT1/BOT/1/68 (AY593845)        EQAERFFKHKLFDWTLDQQFGTTYVLELPTDHKGIYGQLVDSHAYIRNGWDVQVSATATQFGGCLLVAM
SAT2/ZIM/7/83 (AF136607)        EQAERFFKEKLFDWTSDKPFGTLYVLELPKDHKGIYGSLTDAYTYMRNGWDVQVSATSTQFNGGSLLVAM
SAT3/BEC/1/65 (AY593853)        EQAERFFKEKLFTWTASQEFAHVHLLELPTDHKGIYGAMVESHAYVRNGWDVQVSATSTQFNGGTLLVAM 220       230       240       250       260       270       280
                                ....|....|....|....|....|....|....|....|....|....|....|....|....|....|
                                                                                              VP2-193
A/IRN/2/87 fs                   VPEWKEFTQREKYQLTLFPHQFISPRTNMTAHITVPYLGVNRYDQYKKHKPWTLVVMVVSPLTTSS-IAA
mutant strn                     VPEWKKFTQREKYQLTLFPHQFISPRTNMTAHITVPYLGVNRYDQYKKHKPWTLVVMVVSPLTTSS-ISA
O1/BFS1860/UK/67 (AY593816)     VPELCSIQRELYQLTLFPHQFINPRTNMTAHITVPFVGVNRYDQYKHKPWTLVVMVVAPLTVNT-EGA
C3/Resende/BRA/55 (AY593807)    VPEMGDISDREKYQLTLYPHQFINPRTNMTAHITVPYVGVNRYDQYKQHKPWTLVVMVVAPLTVNT-SGA
Asia1/PAK/1/54 (AY593795)       VPELKELDTRQKYQLTLFPHQFINPRTNMTAHINVPFVGVNRYDQYALHKPWTLVVMVVAPLTVKT-GGS
SAT1/BOT/1/68 (AY593845)        VPELCKLDDREKYQLTLFPHQFLNPRTNTTAHIQVPYLGVDRHDQGTRHKAWTLVVMVLAPYTNDQTIGS
SAT2/ZIM/7/83 (AF136607)        VPELCSLKDREEFQLSLYPHQFINPRTNTTAHIQVPYLGVNRHDQGKRHQAWSLVVMVLTPLTTEAQMGS
SAT3/BEC/1/65 (AY593853)        VPELHSLDKRDVSQLTLFPHQYINPRTNTTAHIVVPYVGVNRHDQVQMHKAWTLVVAVMAPLTTSN-MGQ 290       300       310       320       330       340       350
                                ....|....|....|....|....|....|....|....|....|....|....|....|....|....|
A/IRN/2/87 fs                   GQIKVYANIAPTHVHVAGELPSKEGIVPVACSDGYGGLVTTDPKTADPVYGMVYNPPRTNYPGRFTNLLD
mutant strn                     GQIKVYANIAPTHVHVAGELPSKEGIVPVACSDGYGGLVTTDPKTADPVYGMVYNPPRTNYPGRFTNLLD
O1/BFS1860/UK/67 (AY593816)     PQIKVYANIAPTNVHVAGELPSKEGIFVPACADGYGNMVTTDPKTADPAYGKVYNPPRTALPGRFTNYLD
C3/Resende/BRA/55 (AY593807)    QQIKVYANIAPTNVHVAGELPSKEGIFPVACADGYGNMVTTDPKTADPAYGKVYNPPRTALPGRFTNYLD
Asia1/PAK/1/54 (AY593795)       EQIKVYMNAAPTYVHVAGELPSKEGIVPVACADGYGNMVTTDPKTADPVYGKVFNPPRTNLPGRFTNFLD
SAT1/BOT/1/68 (AY593845)        TKAEVYVNIAPTNVYVAGEKPVKQGILPVAVSDGYGGFQNTDPKTSDPVYGHVYNPARTLYPGRFTNLLD
SAT2/ZIM/7/83 (AF136607)        GTVEVYANIAPTNVFVAGEKPAKQGIIPVACFDGYGGFQNTDPKTADPIYGYVYNPSRNDCHGRYSNLLD
SAT3/BEC/1/65 (AY593853)        DNVEVYANIAPTNVYVAGERPSKQGIIPVACNDGYGGFQNTDPKTADPIYGLVSNAPRTAFPGRFTNLLD 360       370       380       390       400       410       420
                                ....|....|....|....|....|....|....|....|....|....|....|....|....|....|
A/IRN/2/87 fs                   VAEACPTLLCFENGKPYVETR-TDDQRLLAKFDVSLAAKHMSNTYLAGIAQYYAQYSGTINLHFMFTGST
mutant strn                     VAEACPTLLCFENGKPYVETR-TDDQRLLAKFDVSLAAKPMSNTYLAGIAQYYAQYSGTINLHFMFTGST
O1/BFS1860/UK/67 (AY593816)     VAEACPTFLHFEGDVPYVTTK-TDSDRVLAQFDMSLAAKHMSNTFLAGLAQYYTQYSGTINLHFMFTGPT
C3/Resende/BRA/55 (AY593807)    VAEACPTFLVFEN-VPYVSTR-TDGQRLLAKFDVSLAARHMSNTYLAGLAQYYTQYAGTINLHFMFTGPT
Asia1/PAK/1/54 (AY593795)       VAEACPTFLRFGE-VPFVKTV-NSGDRLLAKFDVSLAAGHMSNTYLAGLAQYYTQYSGTMNIHFMFTGPT
SAT1/BOT/1/68 (AY593845)        VAEACPTLLDFNG-VPYVQTQSNSGSKVLACFDLAFGHKNMKNTYMSGLAQYFAQYSGTLNLHFMYTGPT
SAT2/ZIM/7/83 (AF136607)        VAEACPTFLNFDG-KPYVVTK-NNGDKVMTCFDVAFTHKVHKNTFLAGLADYYAQYQGSLNYHFMYTGPT
SAT3/BEC/1/65 (AY593853)        VAEACPTFLDFDG-TPYVKTRHNSGSKILAHIDLAFGHKSFKNTYLAGLAQYYAQYSGSINLHFMYTGPT
```

FIG. 9

```
                                    430       440       450       460       470       480       490
                                 ....|....|....|....|....|....|....|....|....|....|....|....|....|....|
A/IRN/2/87 fs                    DSKARYMVAYVPPG--VDTPPDAPERAAHCIHAEWDTGLNSKFTFSIPYMSAADYAYTASDVAETTNVQG
mutant strn                      DSKARYMVAYVPPG--VDTPPDAPERAAHCIHAEWDTGLNSKFTFSIPYMSAADYAYTASDVAETTNVQG
O1/BFS1860/UK/67 (AY593816)      DAKARYMIAYAPPG--ME-PPKTPEAAAHCIHAEWDTGLNSKFTFSIPYLSAADYAYTASDVAETTNVQG
C3/Resende/BRA/55 (AY593807)     DAKARYMVAYVPPG--ME-APENPEEAAHCIHAEWDTGLNSKFTFSIPYISAADYAYTASNEAETTCVQG
Asia1/PAK/1/54 (AY593795)        DAKARYMVAYVPPG--MT-PPTDPERAAHCIHSEWDTGLNSKFTFSIPYLSAADYAYTASDVAEATSVQG
SAT1/BOT/1/68 (AY593845)         NNKAKYMVAYIPPG--THPLPETPEMASHCYHAEWDTGLNSTFTFTVPYISAADYAYTYADEPEQASVQG
SAT2/ZIM/7/83 (AF136607)         HHKAKFMVAYIPPGIETDRLPKTPEDAAHCYHSEWDTGLNSQFTFAVPYVSASDFSYTHTDTPAMATTNG
SAT3/BEC/1/65 (AY593853)         QSKARFMVAYIPPG--TSPVPDTPEKAAHCYHSEWDTGLNSKFTFTVPYMSAADFAYTYCDEPEQASAQG 500       510       520       530       540       550       560
                                 ....|....|....|....|....|....|....|....|....|....|....|....|....|....|
                                             VP3-196              VP3 >< VP1
A/IRN/2/87 fs                    WVCIYQITHGKAEQDTLVVSVSAGKDFELRLPIDPRAQTTATGESADPVTTTVENYGGETQVRRRQHTDV
mutant strn                      WVCIYQITHGKAAQDTLVVSVSAGKDFELRLPIDPRAQTTATGESADPVTTTVENYGGETQVRRRQHTDV
O1/BFS1860/UK/67 (AY593816)      WVCLFQITHGKADGDALVVLASAGKDFELRLPVDARAETTSAGESADPVTTTVENYGGETQIQRRQHTDV
C3/Resende/BRA/55 (AY593807)     WVCVYQITHGKADADALVISASAGKDFELRLPVDARQQTTTTGESADPVTTTVENYGGETQVQRRHHTDV
Asia1/PAK/1/54 (AY593795)        WVCIYQITHGKAEGDALVVSASAGKDFEFRLPVDARQQTTTTGESADPVTTTVENYGGETQTARRLHTDV
SAT1/BOT/1/68 (AY593845)         WVGVYQITDTHEKDGAVIVTVSAGPDFEFRMPISPSRQTTSAGEGADPVTTDASAHGGDTRTTRRAHTDV
SAT2/ZIM/7/83 (AF136607)         WVAVFQVTDTHSAEAAVVVSVSAGPDLEFRFPVDPVRQTTSSGEGADVVTTDPSTHGGAVTEKKRVHTDV
SAT3/BEC/1/65 (AY593853)         WVTLYQITDTHDPDSAVLVSVSAGADFELRLPINPATQTTSAGEGADVVTTDVTTHGGEVSVPRRQHTNV 570       580       590       600       610       620       630
                                 ....|....|....|....|....|....|....|....|....|....|....|....|....|....|
A/IRN/2/87 fs                    SFIMDRFVKINPVT-PTHVIDLMQTHQHALVGALLRAATYYFSDLEIVVRHEGN-LTWVPNGAPEAALSN
mutant strn                      SFIMDRFVKINPVT-PTHVIDLMQTHQHALVGALLRAATYYFSDLEIVVRHEGN-LTWVPNGAPEAALSN
O1/BFS1860/UK/67 (AY593816)      SFIMDRFVKVTPQN-QINILDLMQVPSHTLVGALLRASTYYFSDLEIAVKHEGD-LTWVPNGAPEKALDN
C3/Resende/BRA/55 (AY593807)     AFVLDRFVKVPVSDRQQHTLDVMQVHKDSIVGALLRAATYYFSDLEIAVTHTGK-LTWVPNGAPVSALDN
Asia1/PAK/1/54 (AY593795)        AFVLDRFVKFTPKN--TQTLDLMQIPSHTLVGALLRSATYYFSDLEIALVHTGP-VTWVPNGAPKTALDN
SAT1/BOT/1/68 (AY593845)         TFLLDRFTLVGKTNDNKLVLDLLSTKEKSLVGALLRAATYYFSDLEVACVGTNAWVGWTPNGSPVLTEVG
SAT2/ZIM/7/83 (AF136607)         AFVMDRFTHV-LTNRTAFAVDLMDTNEKTLVGGLLRAATYYFCDLEIACLGEHERVWWQPNGAPRTTTLR
SAT3/BEC/1/65 (AY593853)         EFLLDRFTHVGKVNES-RTISLMDTKEHTLVGAILRSATYYFCDLEVAILGTAPWAAWVPNGCPHTGRVE 640       650       660       670       680       690       700
                                 ....|....|....|....|....|....|....|....|....|....|....|....|....|....|
A/IRN/2/87 fs                    TSNPTAYHKEPFTRLALPYTAPHRVLATVYNGTNKYAATGA-----RRGDLGSLAA----RVAAQLPSSF
mutant strn                      TSNPTAYHKEPFTRLALPYTAPHRVLATVYNGTNKYAATGD-----SRGDLGPLAA----RVAAQLPSSF
O1/BFS1860/UK/67 (AY593816)      TTNPTAYHKAPLTRLALPYTAPHRVLATVYNGECRYSRNAVP---NLRGDLQVLAQ----KVARTLPTSF
C3/Resende/BRA/55 (AY593807)     TTNPTAYHKGPLTRLALPYTAPHRVLATTYTGTTTYTTSAR------RGDSAHLAA----AHARHLPTSF
Asia1/PAK/1/54 (AY593795)        QTNPTAYHKQPITRLALPYTAPHRVLATVYNGKTTYGEEPT-----MRGDRAVLAS----KVNKQLPTSF
SAT1/BOT/1/68 (AY593845)         D-NPVVFSRRGTTRFALPYTAPHRVLATVYNGDCKYKPTGTAPRENIRGDLATLAARIASETH--IPTTF
SAT2/ZIM/7/83 (AF136607)         D-NPMVFSHNNVTRFAVPYTAPHRLLSTRYNGECKYTQQSTA----IRGDRAVLAAKYANTKHK-LPSTF
SAT3/BEC/1/65 (AY593853)         D-NPVVHSKGSVVRFALPYTAPHGVLATVYNGNCKYSETQRVTS--RRGDLAVLAQRVENETTRCLPTTF 710       720       730       740       750
                                 ....|....|....|....|....|....|....|....|....|
                                                                        VP1 >
A/IRN/2/87 fs                    NFGAIRATTIHELLVRMRRAELYCPRPLLA-MEVSAEGRHKQKIIAPAKQ
mutant strn                      NFGAIRATTIHELLVRMRRAELYCPRPLLA-MEVSAEGRHKQKIIAPAKQ
O1/BFS1860/UK/67 (AY593816)      NYGAIKATRVTELLYRMKRAETYCPRPLLA-IHPTEA-RHKQKIVAPVKQ
C3/Resende/BRA/55 (AY593807)     NFGAVKAETVTELLVRMKRAELYCPRPILP-IQPTGD-RHKQPLIAPAKQ
Asia1/PAK/1/54 (AY593795)        NYGAVKAENITEMLIRIKRAETYCPRPLLA-LDTTQD-RRKQEIIAPEKQ
SAT1/BOT/1/68 (AY593845)         NYGMIYTQAEVDVYLRMKRAELYCPRPVLTHYDHNGRDRYKTTLVKPAKQ
SAT2/ZIM/7/83 (AF136607)         NFGHVTADKPVDVYYRMKRAELYCPRPLLPGYDHADRDRFDS-PIGVEKQ
SAT3/BEC/1/65 (AY593853)         NFGRLLCE-EGDAYYRMKRAELYCPRPLRVRYTHT-TDRYKTPLVKPDKQ
```

FOOT AND MOUTH DISEASE VIRUS WITH INCREASED STABILITY AND ITS USE AS VACCINE

CROSS-REFERENCE TO RELATED APPLICATIONS

This application is the U.S. National Phase of International Application No. PCT/GB2011/051678, incorporated by reference, filed Sep. 8, 2011, which claims the priority benefit of Great Britain Patent Application No. 1014965.6, filed Sep. 8, 2010.

FIELD OF THE INVENTION

The present invention relates to a foot and mouth disease virus (FMDV) comprising one or more amino acid mutations and having improved stability compared to the wild-type virus of the same subtype. The virus entity may be used as, or as part of, an FMD vaccine.

BACKGROUND TO THE INVENTION

Foot and Mouth Disease (FMD)

FMD is a highly contagious and economically devastating disease of cloven-hoofed animals (Artiodactyla), affecting domesticated ruminants, pigs and a large number of wildlife species (Alexandersen et al., (2003) Journal of Comparative Pathology 129:1-36) of which the causal agent is Foot-and-Mouth Disease Virus (FMDV).

FMDV is a positive sense, single stranded RNA virus and is the type species of the Aphthovirus genus of the Picornaviridae family. FMDV exists as seven antigenically distinct serotypes namely A, O, C, Asia 1 and South African Territories (SAT) 1, 2 and 3, with numerous subtypes within each serotype. With the exception of New Zealand, outbreaks have been recorded in every livestock-containing region of the world and the disease is currently enzootic in all continents except Australia and North America. Although mortality rates are generally low (less than 5%) in adult animals, the UK 2001 FMD Pan-Asian O outbreak clearly identifies the serious economic consequences associated with the disease, with the cost to the public sector estimated at over 4.5 billion euros and the cost to the private sector at over 7.5 billion euros (Royal Society Report (2002) on Infectious Disease in Livestock-Scientific questions relating to the transmission, prevention and control of epidemic outbreaks of infectious disease in livestock in Great Britain. (2002) Latimer Trend Limited, Cornwall, UK).

FMD is ranked first in the l'Office International des Epizooties (OIE, World Organisation for Animal Health) list of notifiable diseases, which by definition, means that it has the potential for rapid and extensive spread within and between countries. Thus, current intensive farming practices and high stocking densities clearly encourage the rapid spread of such a disease.

FMD is widely distributed throughout the world. Developed regions such as the continents of North and Central America and Antarctica, and countries such as Australia and New Zealand are free from disease while FMD is endemic in many developing countries such as those in sub-Saharan Africa, the Middle East, southern Asia, Southeast Asia and South America. There are also some areas of the world which are normally free from disease, such as Europe where FMD was eradicated in 1989 and where vaccination has ceased since 1991. However, there have been occasional incursions of disease such as the 2001 UK/EIRE/France/Netherlands epidemic due to a PanAsian O strain (Knowles et al., (2001) Veterinary Record. 148. 258-259) and the 2007 UK outbreak of serotype O1 BFS/1967.

Conventional vaccines against FMD consist of whole virus virions that have been chemically inactivated, normally by use of an aziridine such as binary ethyleneimine (BEI). More than a billion doses are used annually worldwide (Rweyemamu and Le Forban (1999) Advances in Virus Research. 53. 111-126) and in many countries have been utilised successfully in controlling the disease.

Capsid Stability

Conventional formulated FMD vaccines need to be stored at 4° C. and have an expected shelf life of at most 12-18 months.

Capsid stability is disrupted by both pH and temperature with temperatures above 56° C. and a pH below 6.8 or above 9.0 believed to result in inactivation of the virus due to dissociation of the intact 146S particle into 12S particles.

A problem associated with current FMD vaccines is thus their limited thermostability and their reliance on a good cold-chain along with appropriate diluents and excipients. There is therefore a need for improved FMD vaccines.

DESCRIPTION OF THE FIGURES

FIG. 6—Alignment of predicted amino acid sequences of the P1 capsid of A/IRN/2/87 (field isolate) (SEQ ID NO: 3) and mutant vaccine strain. Dots indicate the amino acid is identical to A/IRN/2/87; a dash indicates an amino acid deletion compared to A/IRN/2/87. Cleavage sites between the mature polypeptides, VP4, VP2, VP3 and VP1, are indicated.

FIG. 9—An alignment of the seven main FMDV serotypes, highlighting the residues which are equivalent to the following residues in FMDV A strain:
VP2—A193S; L78S; E79A; K80R; E131K; and T88A.
VP3—H85P; and E196A.
A/IRN/2/87 fs (SEQ ID NO: 4); mutant strn (SEQ ID NO: 5); O1/BFS1860/UK/67 (AY593816) (SEQ ID NO: 6); C3/Resende/BRA/55 (AY593807) (SEQ ID NO: 7); Asia1/PAK/1/54 (AY593795) (SEQ ID NO: 8); SAT1/BOT/1/68 (AY593845) (SEQ ID NO: 9); SAT2/ZIM/7/83 (AF136607) (SEQ ID NO: 10); SAT3/BEC/1/65 (AY593853) (SEQ ID NO:11).

SUMMARY OF ASPECTS OF THE INVENTION

Figure 1A:
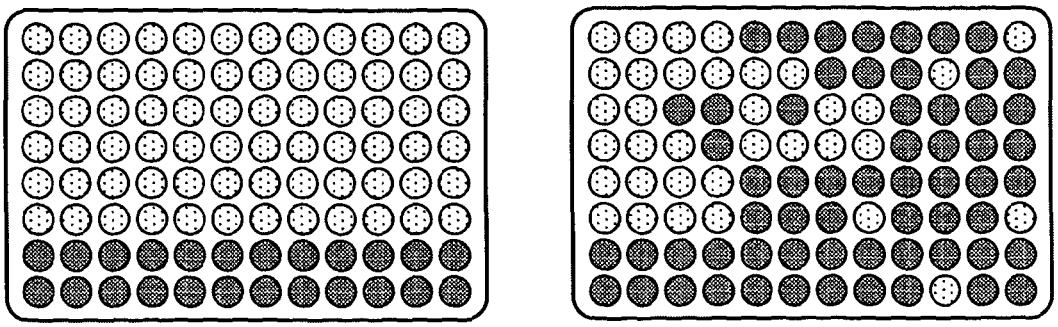
FIG. 1—A comparison of cell death following treatment with virus previously incubated at 4° C. a) field isolate; b) mutant virus FIG. 2—A comparison of cell death following treatment with virus previously incubated at 50° C. a) field isolate; b) mutant virus FIG. 3—A comparison of cell death following treatment with virus previously incubated at 55° C.: Top row of plates—field isolate; Bottom row of plates—mutant virus FIG. 4—A comparison of cell death following treatment with virus previously incubated at 60° C. a) field isolate; b) mutant virus FIG. 5—Summary of viral titre observed following heat treatment.
Figure 1B:
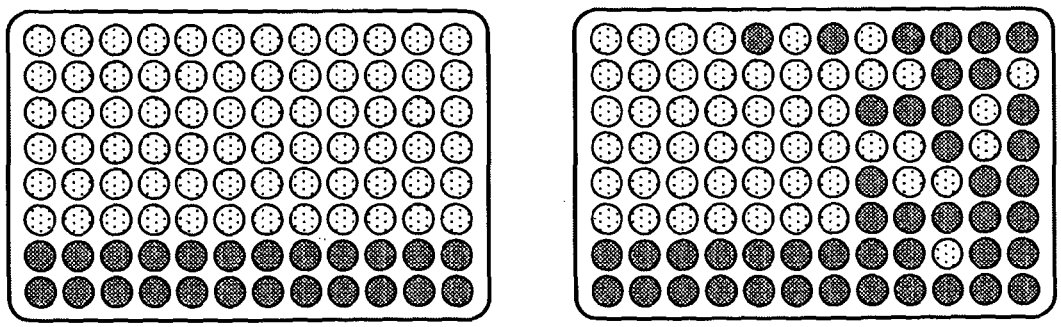
Figure 2A:
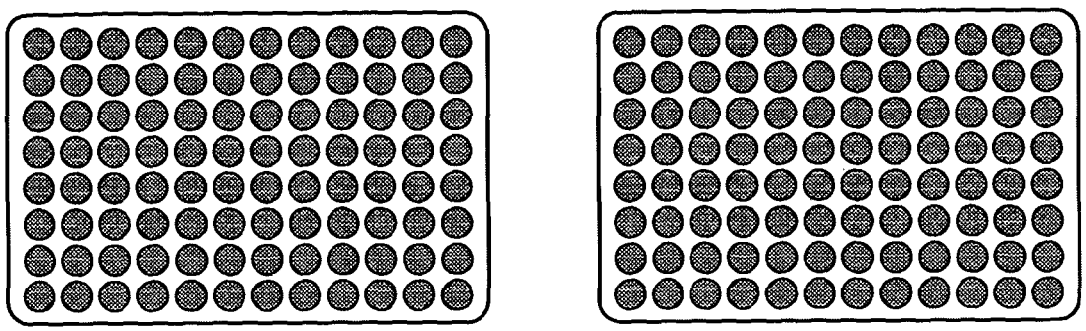
Figure 2B:
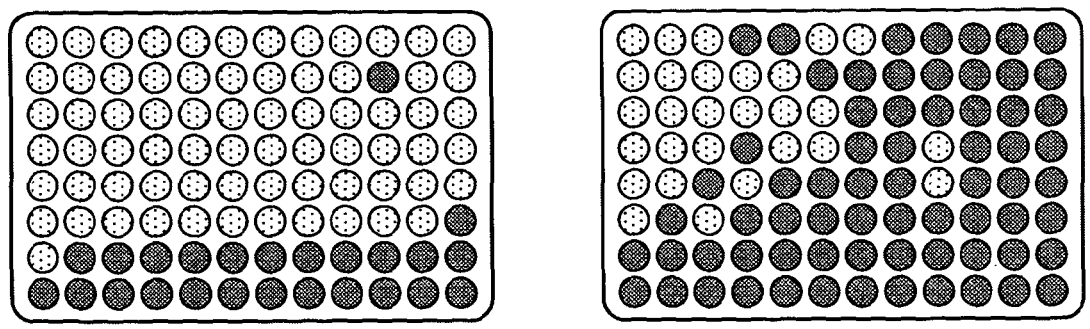
Figure 3:
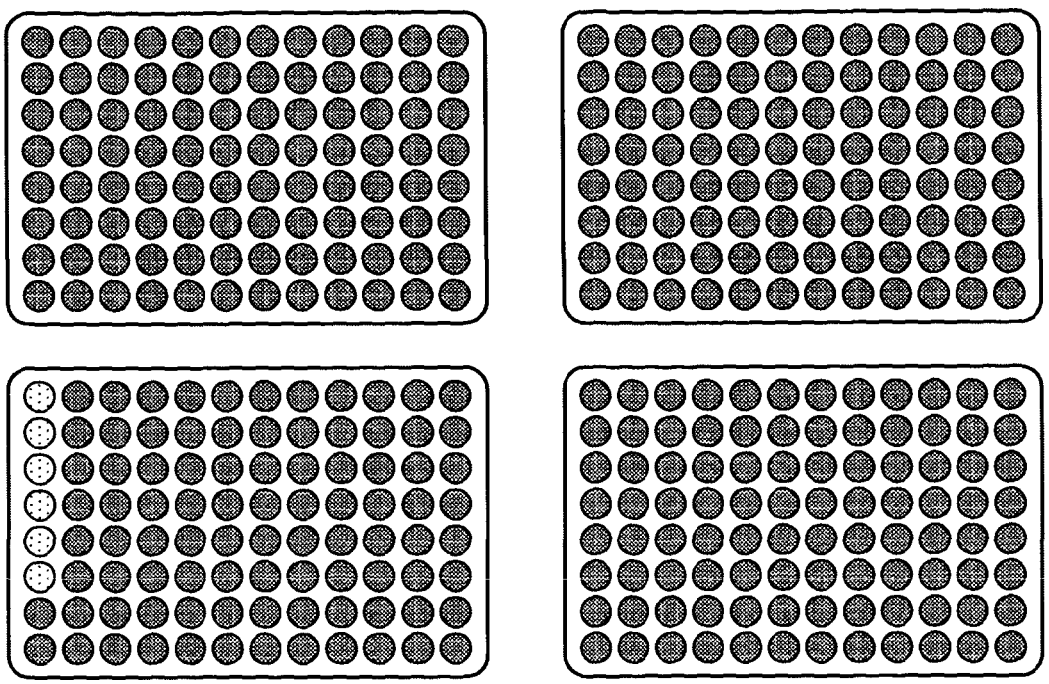
Figure 4A:
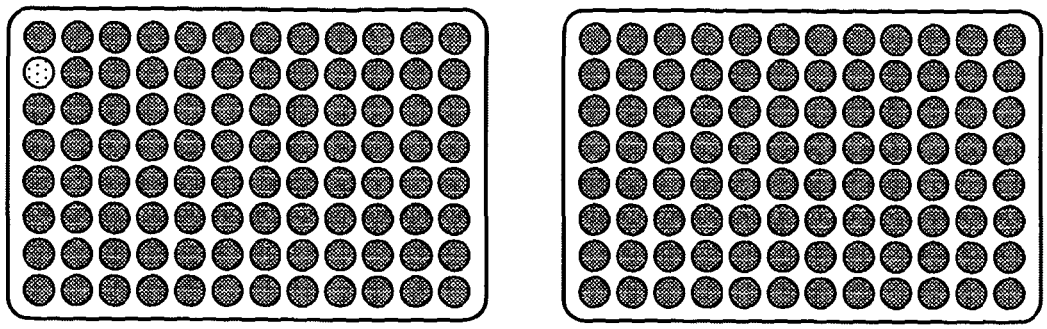
Figure 4B:
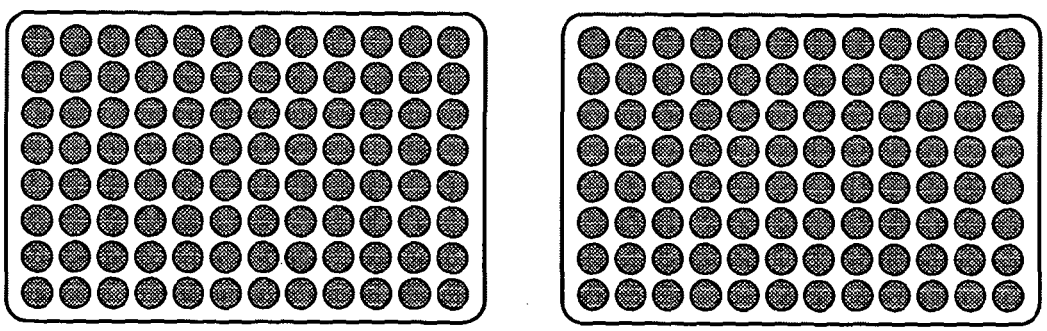

The present inventors have surprisingly found that it is possible to improve the stability of FMDV by mutation of one or more key amino acid residues along one of the axes of symmetry of the capsid structure.

Thus, in a first aspect, the present invention provides a foot and mouth disease (FMD) virus having improved stability compared to the field isolate of the same subtype, wherein the virus comprises one or more amino acid mutations along a line of symmetry of the capsid structure.

The FMDV may have one or more of the following mutations in VP2: A193S; L78S; E79A; K80R; E131K; T88A, with reference to the position numbering of VP2 from A strain FMDV having the amino acid sequence shown as SEQ ID NO: 1.

The FMDV may have one or more of the following mutations in VP3: H85P; E196A with reference to the position numbering of VP3 from A strain FMDV having the amino acid sequence shown as SEQ ID NO: 2.

The FMDV may have one or more of the following mutations: E196A in VP3 with reference to the position numbering of VP3 from A strain FMDV having the amino acid sequence shown as SEQ ID NO: 2; A193S and/or T88A in VP2 with reference to the position numbering of VP2 from A strain FMDV having the amino acid sequence shown as SEQ ID NO: 1.

The FMDV may be based on an FMDV A strain.

The FMDV may be obtained by introducing one or more mutations into an FMDV field isolate or vaccine strain.

The FMDV may have improved thermostability, pH stability and/or protease stability compared to the field isolate of the same subtype.

In a second aspect, the present invention provides a foot and mouth disease vaccine comprising an FMDV according to the first aspect of the invention.

The vaccine may be used for preventing foot and mouth disease in a subject.

In a third aspect the present invention provides a method of preventing foot and mouth disease in a subject which comprises the step of administrating a vaccine according to the second aspect of the invention to the subject.

In a fourth aspect the present invention provides a method for improving the stability of an FMDV which comprises the step of introducing one or more amino acid substitutions along a line of symmetry of the capsid structure.

Capsid stability is believed to be regulated by three main events i) the grouping together of VP3 N-termini which results in the formation of a β-annulus at the 5-fold axis holding the protomers (VP1-4) together, ii) clustering of myristol groups at the base of the 5-fold axis and iii) the presence of disulphide bonds linking the VP3 N-termini.

The vaccine of the present invention having increased thermostability has several commercial and manufacturing benefits including:
a) a considerably extended shelf-life;
b) less reliance on the cold-chain requirement;
c) greater versatility for such antigens to be incorporated into delivery systems and/or used with other adjuvants or vaccine components; and
d) the capacity to produce a better and more durable immune response.

DETAILED DESCRIPTION

Foot and Mouth Disease (FMD)

Foot-and-Mouth. Disease (FMD) is an acute systemic disease of cloven-hoofed animals of which the causal agent is Foot-and-Mouth Disease virus (FMDV). FMDV is a positive sense RNA virus which when translated results in the production of both structural and non structural proteins with 60 copies of structural proteins VP1-VP4 associating to form the icosahedral capsid surrounding the viral genome.

The disease is characterised by high fever for two or three days followed by the formation of blisters or lesions inside the mouth, on the mammary glands of females and also on the feet. The vesicles generally rupture within 1-2 days resulting in the formation of sore open wounds which if located on the feet cause lameness. Frequently, the healing of lesions is delayed by secondary bacterial infection of the wounds. Though most animals eventually recover from FMD, the disease can lead to myocarditis and death, especially in newborn animals. The long-term welfare of survivors can be poor, with many suffering secondary consequences such as mastitis, endometritis, chronic lameness and a substantial drop in milk yield (The Royal Society Report, (2002) as above).

The virus is present in secretions such as faeces, saliva, milk and breath and can infect susceptible animals through inhalation, ingestion, skin trauma and contact with mucosal membranes. Cattle, sheep and goats predominantly contract disease via the respiratory tract, whereas pigs are considerably less susceptible to aerosol infections requiring up to 600 times more tissue culture infectious doses (TCID50) of virus to become infected and therefore generally contract disease through ingestion (Donaldson and Alexandersen, (2002) Revue Scientifique et Technique Office International des Epizooties. 21. 569-575).

Following infection, the incubation period between infection and the appearance of clinical signs ranges from two to eight days but in some cases has been reported to be as long as 14 days (Alexandersen et al., (2003) as above). The severity of clinical signs is related to infectious dose, species, the level of immunity and the virus strain. It is sometime difficult to differentiate FMD clinically from other vesicular diseases, such as swine vesicular disease, vesicular stomatitis and vesicular exanthema. Laboratory diagnosis of any suspected FMD case is therefore usually necessary. The demonstration of specific antibodies to FMDV structural proteins in non-vaccinated animals, where a vesicular condition is present, is considered sufficient for a positive diagnosis.

The preferred procedure for the detection of FMDV antigen and identification of viral serotype is the ELISA. The test recommended by the World Organisation of Animal health is an indirect sandwich test in which different rows in multiwell plates are coated with rabbit antisera to each of the seven serotypes of FMD virus. These are the 'capture' sera. Test sample suspensions are added to each of the rows, and appropriate controls are also included. Guinea-pig antisera to each of the serotypes of FMD virus are added next, followed by rabbit anti-guinea-pig serum conjugated to an enzyme. A colour reaction on the addition of enzyme substrate, in the presence of a chromogen, indicates a positive reaction.

Alternatively, it is possible to use nucleic acid recognition methods to detect foot and mouth disease. Reverse transcription polymerase chain reaction (RT-PCR) can be used to amplify genome fragments of FMDV in diagnostic materials including epithelium, milk, and serum. RT combined with real-time PCR has a sensitivity comparable to that of virus isolation. Specific primers can be designed to distinguish between FMDV serotypes.

Foot and Mouth Disease Virus (FMDV)

Foot and mouth disease virus (FMDV) is a positive sense, single stranded RNA virus and is the type species of the Aphthovirus genus of the Picornaviridae family. The virus is packaged in an icosahedral symmetric protein shell or capsid, approximately 28-30 nm in diameter. The capsid is composed of 60 copies each of four viral structural proteins, VP1, VP2, VP3 and the internally located VP4. VP1, 2 and 3 have similar tertiary structures containing a highly conserved β-barrel core. (Acharya et al., (1989) Nature. 337. 709-716). The FMDV RNA genome consists of an open reading frame encoding the four structural proteins, and at least eight non-structural proteins (NSP) (Leader, 2A, 2B, 2C, 3A, 3B, 3 Cpro, 3Dpol).

FMDV exists as seven antigenically distinct serotypes, namely 0, A, C, SAT-1, SAT-2, SAT-3, and Asia-1, with numerous subtypes within each serotype. These serotypes show some regionality, and the 0 serotype is most common.

FMDV multiplication occurs in the cytoplasm of the host cell. The virus enters the cell through a specific cell surface receptor. FMDV favours the use of a class of receptors known as integrins for cell entry, but when the virus is tissue culture adapted it has been found to adapt to use an alternative receptor class to infect cells (Baranoski et al., (2000) Journal of Virology. 74. 1641-1647 and Baxt and Bachrach, (1980) Virology. 104. 391-405).

Vaccine

The term 'vaccine' as used herein refers to a preparation which, when administered to a subject, induces or stimulates a protective immune response. A vaccine can render an organism immune to a particular disease, in the present case FMD.

The vaccine may be used prophylactically, to block or reduce the likelihood of FMDV infection and/or prevent or reduce the likelihood of contracting FMD.

The vaccine may comprise one or more vaccinating entity (ies) and optionally one or more adjuvants, excipients, carriers or diluents.

One of the advantages of the present invention is the versatility afforded by improved antigen stability in terms of vaccine adjuvants and delivery systems. The FMDV of the present invention may, for example, be used with adjuvants and/or delivery systems which are unsuitable for storage at 4° C. Some adjuvants, such as oil adjuvants for making emulsions, are ideally blended at room temperature or higher. This is not suitable for traditional FMD vaccines, but are suitable for the more stable vaccines of the present invention.

The FMDV of the present invention may be incorporated into a delivery system which allow slow release of antigen over time. For example, the FMDV may be microencapsulated. Some known microencapsulation materials are made from a polymer based on lactic acid. This can result in a localised low pH around the site of the microcapsule which is unsuitable for traditional FMD vaccine antigens. The FMDV of the present invention, having increased resistance to pH, may be suitable for administration by this route.

The vaccine may also comprise, or be capable of expressing, another active agent, for example one which may stimulate early protection prior to the vaccinating entity-induced adaptive immune response. The agent may be an antiviral agent, such as type I interferon. Alternatively, or in addition, the agent may be granulocyte-macrophage colony-stimulating factor (GM-CSF).

The vaccine may also comprise, or be capable of expressing, the FMDV non-structural protein 3D as a separate entity. The 3D protein has been shown to stimulate a strong humoral and cellular immune response in the host.

Vaccinating Entity

The term 'vaccinating entity' as used herein is used to refer to the active component of a vaccine, which triggers an adaptive anti-FMDV immune response. Upon administration to a subject, the presence of the active component stimulates antibody production or cellular immunity against FMDV.

The vaccinating entity of the present invention may be an inactivated, dead or attenuated form of FMDV.

The term 'inactivated' is used to describe a virus which has effectively lost the ability to replicate and cause infection.

Current commercially available FMD vaccines commonly contain chemically inactivated FMDV as the vaccinating entity. The virus may be inactivated by, for example, treatment with aziridines such as binary ethyleneimine (BEI). The virus used is usually a seed virus strain derived from cell culture, which, once inactivated, is then blended with suitable adjuvant/s and excipients. Two categories of chemically inactivated vaccine are currently available, namely water based and oil based vaccines (either single, double or complex oil emulsions). Water based vaccines, which are normally adjuvanted with aluminium hydroxide and saponin, are used for cattle, sheep and goats, whereas oil based vaccines, which induce more versatile and longer lasting immunity, can be used for all target species, including pigs.

A vaccine of the present invention, comprising inactivated FMDV having one or more amino acid substitutions along a line of symmetry of the capsid structure, can be produced in the same way as traditional vaccines. It can be produced in the same production plants as previously used for traditional vaccines, involving minimal change in production technology or technique.

Stability

The present invention relates to a foot and mouth disease virus having improved stability compared to the field isolate of the same subtype. The FMD virus may, for example, have improved thermostability, pH stability and/or protease stability compared to the field isolate of the same subtype.

Thermostability is an increased stability of the virus to temperature. Thermostability may be measured in terms of the effect of a given temperature for a given period on viral integrity and/or infectivity. For example, viral denaturation and/or the effect of temperature on viral titre may be investigated.

Virus titre may be measured by methods known in the art, such as by investigating the capacity of a viral preparation to kill a given cell type. For example, one can investigate the capacity of a viral preparation to prevent formation of a cell monolayer, as described in the Examples.

The mutant virus may have improved stability at cool storage temperatures, for example about 4° C., or at ambient temperatures, for example between 15-30° C.

The mutant virus may have improved stability in vivo, for example at temperatures of about 37° C. A vaccine comprising the virus may have improved half-life following administration to a subject.

The mutant virus may have improved stability following exposure to a period of high temperature than the field isolate of the same subtype. The mutant virus may thus be more resistant to temporary "temperature abuse" than the field isolate. The mutant virus may, for example, have improved stability following a period of exposure to a temperature of 40, 45, 50 or 55° C.

The mutant virus may have titre or half-life which is 1.5, 2, 5 or 10× that of the field isolate of the same subtype.

The mutant virus may exhibit stability within a pH range greater than pH 6-9.

The mutant virus may have improved protease stability compared to the field isolate. This may be due to a reduction in the number of available protease cleavage sites.

Mutation

The present invention relates to a foot and mouth disease virus having one or more amino acid mutations.

The amino acid mutation(s) may result in improved capsid stability.

The mutation may be an amino acid substitution.

The mutation may reduce the number of available protease cleavage sites.

The mutation may be along a line of symmetry of the capsid structure.

As explained above, FMDV comprises 60 copies each of four structural proteins, termed VP1, VP2, VP3, and VP4, which encapsidate a single, positive-sense RNA genome. The proteins form a pseudo T=3 icosahedral capsid with VP1 located close to the fivefold axes of symmetry and VP2 and VP3 alternating around the threefold axes (Fry et al (2005) Curr. Top. Microbiol. Immunol. 288:71-101). VP4, which is myristoylated at the N terminus, is an internal component of the capsid.

Figures 7A, 7B:
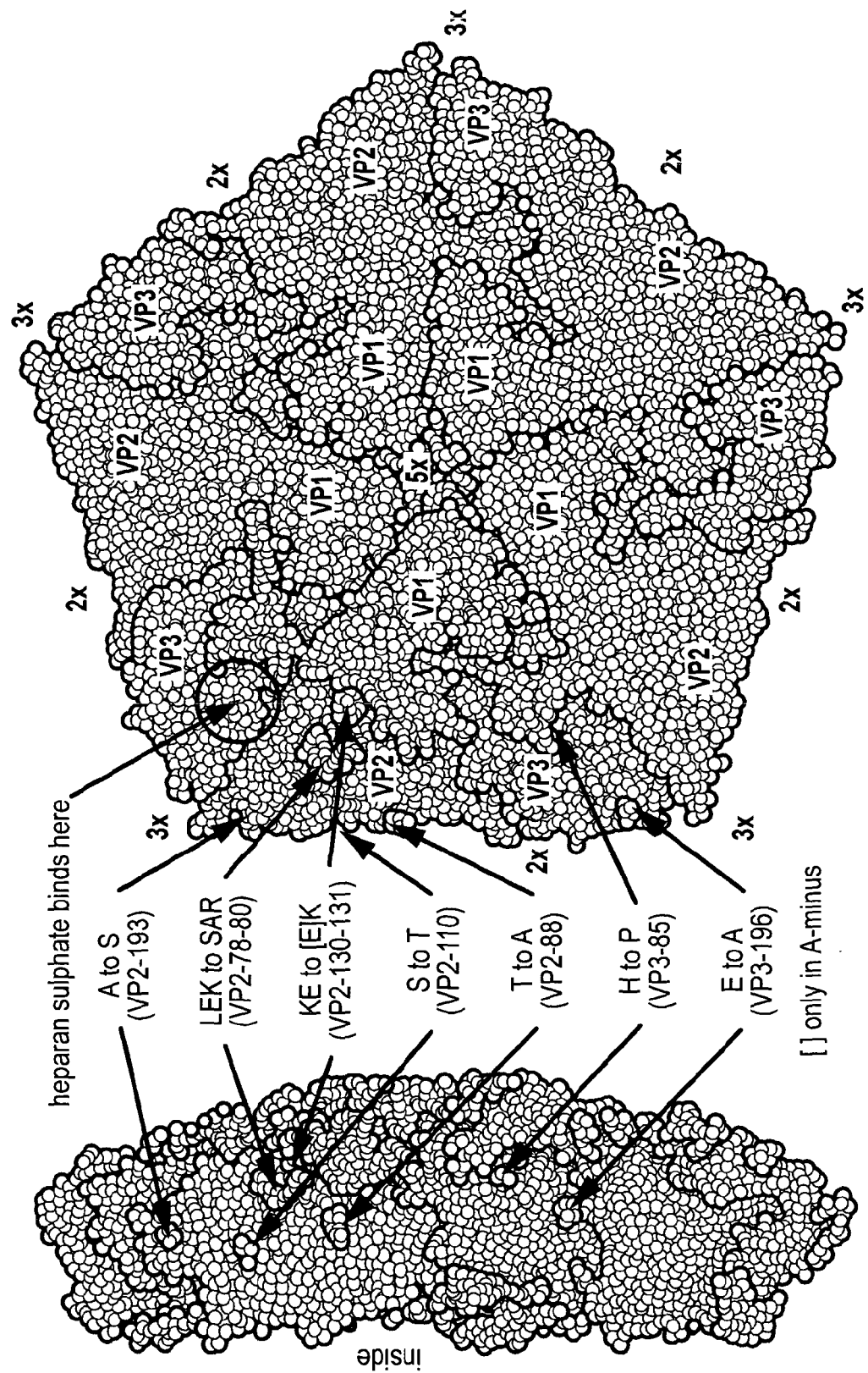
FIG. 7—Model showing amino acid sequence differences between A/IRN/2/87 (field isolate) and mutant strain. Axes of symmetry are indicated as 5x, 3x and 2x. a) edge view; b) face view.
Figure 8:
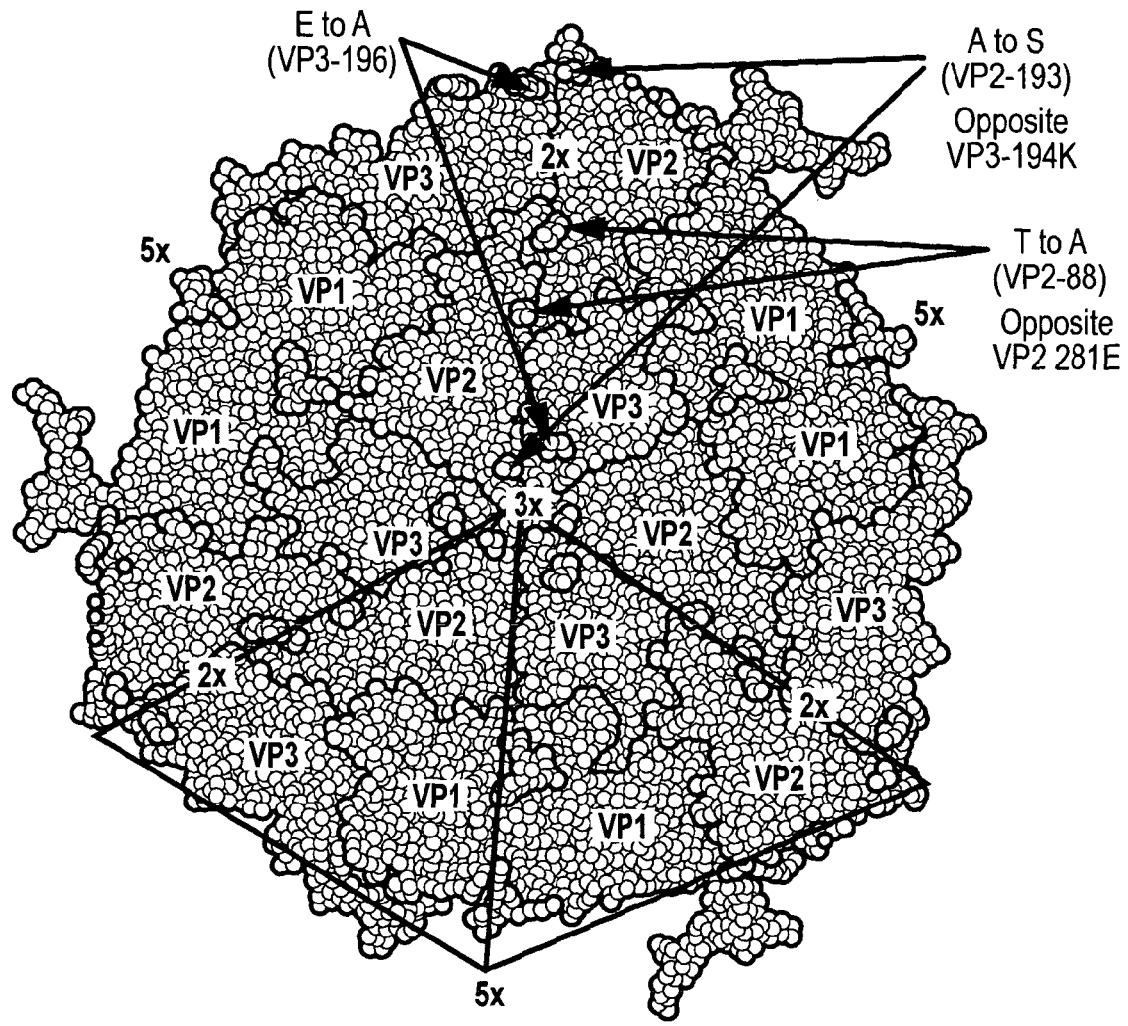
FIG. 8—Model showing amino acid sequence differences between A/IRN/2/87 (field isolate) and mutant strain. Axes of symmetry are indicated as 5x, 3x and 2x. Only changes close to the 2x axis of symmetry are shown.

FIGS. 7 and 8 show the 5x, 3x and 2x axes of symmetry. The mutation may lie along the 2x axis of symmetry. A mutation may be considered to lie along the axis if it is positioned within 20, 10 or 5 Å from the line of symmetry.

The virus may also comprise one or more amino acid mutations which are removed from a line of symmetry of the capsid structure. For example, the virus may comprise a deletion of one or a plurality of amino acids. Such a deletion may reduce the number of protease cleavage sites available.

The deletion may involve total or partial removal of the VP1 G-H loop. For example the deletion may involve removal of seven or more amino acid residues from the G-H loop, including the RGD motif, such as between 7 and 30 amino acids. The VP1 loop is found in the section from amino acid 129 to amino acid 172 of the VP1 polypeptide. The deletion may involve removal of all or a part of this 30 amino acid section.

Substitutions

The FMD virus of the present invention varies from the field isolate of the same subtype by including one or more mutations. In other words, the sequence of the mutant FMDV is different from the field isolate at one or more positions or residues. The mutations may be amino acid substitutions, that is, a change of one amino acid residue for another.

In describing the mutant FMD virus, the following nomenclature will be used: [amino acid in field isolate/position according to the numbering system/substituted amino acid]. Accordingly, for example, the substitution of alanine with proline in position 141 is designated as A141P. Multiple mutations may be designated by being separated by slash marks "/", e.g. A141P/G223A representing mutations in position 141 and 223 substituting alanine with proline and glycine with alanine respectively.

The mutation(s) may be in any of the capsid structural proteins, namely VP1, VP2, VP3 or VP4. The mutation(s) may be in VP2 and/or VP3.

With regard to VP2, the positions referred to herein by numbering relate to the numbering of a VP2 from an A strain FMD from the field isolate A/IRN/2/87. This reference sequence is shown below (SEQ ID NO: 1):

DKKTEETTLLEDRILTTRNGHTTSTTQSSVGVTYGYSTGEDHVSGPNTSG

LETRVVQAERFFKKHLFDWTPDKPFGHLEKLELPTEHTGVYGHLVESFAY

MRNGWDVEVSAVGNQFNGGCLLVAMVPEWKEFTQREKYQLTLFPHQFISP

RTNMTAHITVPYLGVNRYDQYKKHKPWTLVVMVVSPLTTSSIAAGQIKVY

ANIAPTHVHVAGELPSKE

The FMD virus of the present invention may have one or more of the following mutations in VP2: A193S; L78S; E79A; K80R; E131K; T88A, with reference to the position numbering of VP2 from A strain FMDV having the amino acid sequence shown as SEQ ID NO: 1.

The FMD virus of the present invention may have either or both of the following mutations in VP2: A193S and/or T88A.

The FMD virus of the present invention may comprise two, three, four or five of the following mutations in VP2: A193S; L78S; E79A; K80R; E131K; T88A. The FMD virus of the present invention may comprise all of the following mutations in VP2: A193S; L78S; E79A; K80R; E131K; T88A.

With regard to VP3, the positions referred to herein by numbering relate to the numbering of a VP3 from an A strain FMD from the field isolate A/IRN/2/87. This reference sequence is shown below (SEQ ID NO: 2):

GIVPVACSDGYGGLVTTDPKTADPVYGMVYNPPRTNYPGRFTNLLDVAEA

CPTLLCFENGKPYVETRTDDQRLLAKFDVSLAAKHMSNTYLAGIAQYYAQ

YSGTINLHFMFTGSTDSKARYMVAYVPPGVDTPPDAPERAAHCIHAEWDT

GLNSKFTFSIPYMSAADYAYTASDVAETTNVQGWVCIYQITHGKAEQDTL

VVSVSAGKDFELRLPIDPRAQ

The FMD virus of the present invention may have either or both of the following mutations in VP3: H85P; E196A, with reference to the position numbering of VP3 from A strain FMDV having the amino acid sequence shown as SEQ ID NO: 2.

The FMD virus of the present invention may comprise one or more of the following mutations: E196A in VP3 with reference to the position numbering of VP3 from A strain FMDV having the amino acid sequence shown as SEQ ID NO: 2; A193S and/or T88A in VP2 with reference to the position numbering of VP2 from A strain FMDV having the amino acid sequence shown as SEQ ID NO: 1.

The numbering system, even though it may use a specific sequence as a base reference point, is also applicable to all relevant homologous sequences. For example, the position numbering may be applied to homologous sequences from other field isolates and/or other FMDV strains, subtypes or serotypes. For example, the position numbering may be applied to VP2 and/or VP3 sequences from O, C, SAT-1, SAT-2, SAT-3, or Asia-1 FMDV serotypes.

It is possible to align the VP2 and VP3 sequences from all FMDV virus strains, subtypes and serotypes, in order to obtain equivalent position numbering. FIG. 9 provides an alignment of the seven main FMDV serotypes, highlighting the residues which are equivalent to the following residues in FMDV A strain:

VP2—A193S; L78S; E79A; K80R; E131K; and T88A.
VP3—H85P; and E196A.

The present invention also provides nucleic acid sequences capable of encoding mutant VP2, VP3 or FMD virus as described herein. In view of the relationship between nucleic acid sequence and polypeptide sequence, in particular, the genetic code and the degeneracy of this code, it is possible to design and produce such nucleic acid sequences without difficulty. For each amino acid substitution in the FMDV mutant structural protein sequence, there may be one or more codons which encode the substitute amino acid.

Mutations in amino acid sequence and nucleic acid sequence may be made by any of a number of techniques, as known in the art. Mutations may, for example, be introduced into field isolate or wild-type sequences by means of PCR (polymerase chain reaction) using appropriate primers.

The mutant polypeptides, viruses and nucleic acids may be produced by any suitable means known in the art. Specifically, they may be expressed from expression systems, which may be in vitro or in vivo in nature. Mutant polypeptides may, for example be expressed using plasmids and/or expression vectors comprising the relevant nucleic acid sequences. Mutant viruses may be produced from producer cells using procedures known in the art. The present invention also encompasses such expression systems and transformed cells.

Field Isolate

The mutant FMD virus of the present invention may be derivable from a "field isolate" virus. A field isolate is a naturally occurring strain of FMDV, for example one isolated from a real-life FMDV outbreak or endemic FMDV infection.

For a mutant virus according to the present invention, the relevant field isolate is the one which has the highest degree of sequence identity at the amino acid level over the entire P1 capsid sequence.

Method

The present invention also provides a method for improving the stability of an FMD virus or vaccine which comprises the step of introducing one or more mutations along a line of symmetry of the capsid structure.

The mutant virus may, for example, have improved thermostability, pH stability or protease resistance.

The mutation(s) may be an amino acid substitution. Techniques for introducing amino acid mutations are known in the art, such as site directed mutagenesis and PCR modification of the encoding nucleic acid.

Improved stability compared to the parent strain (i.e. the FMDV before mutation) may be ascertained and measured using methods known in the art, such as those which investigate the integrity and/or infectivity of the virus. The stability of an FMD virus, especially an uninfectious FMD vaccinating entity, may be investigated by looking at denaturation rather than infectivity. Inactivated virus is commonly checked for stability by the use of sucrose density gradient centrifugation and the measure of intact 146S antigen. Alternatively and ELISA-based system may be used.

The invention will now be further described by way of Examples, which are meant to serve to assist one of ordinary skill in the art in carrying out the invention and are not intended in any way to limit the scope of the invention.

EXAMPLES

Example 1

Comparing the Thermostability of a Field Isolate FMDV a Strain with a Mutant FMDV a Strain Virus (800 ul) was added neat to a PCR 96 well plate (100 ul per well) in every well of one column. The field isolate (A Iran 2/87) was aliquoted into column 1, A+ was aliquoted in column 4 and A- was aliquoted in column 8 of each PCR plate. One PCR plate was assembled for each temperature. PCR plates were then sealed and incubated at the appropriate temperature for 1 hour. For 4° C. this was done in a fridge whereas for 50° C., 55° C. and 60° C. this was done using a PCR machine (Veriti thermocycler).

Whilst the virus was incubating, 100 ul of media was added to all wells (except the first column, rows A-F) on a 96 well cell culture plate. Rows G and H were no virus controls and thus also had 100 ul of media added to them. Two plates were prepared for each temperature.

Following 1 hour incubation, 100 ul of heat treated virus was added to the first column and titrated 2-fold across the plates. Rows G and H were no virus controls. 50 ul of $1 \times 10^6$ RS cells were then added to the plates. Plates were sealed and incubated at 37° C. for 72 hours. Plates were then stained with plate stain (Napthalene black powder 0.4% w/v in physiological saline containing 2% w/v citric acid crystals).

Each dilution step has a maximum of eight wells where the cells can form into a monolayer. If each individual well contains sufficient infectious virus particles, cell death will occur and no cell monolayer will form. Virus titre is calculated as follows:

8 wells exhibiting 100% cpe at virus log. dilution $10^{-4.9}$
7 wells exhibiting 100% cpe at virus log. dilution $10^{-5.2}$
4 wells exhibiting 100% cpe at virus log. dilution $10^{-5.5}$
1 well exhibiting 100% cpe at virus log. dilution $10^{-5.8}$ $$\frac{\text{Total number of wells exhibiting 100\% } cpe}{\text{no. of wells/dilution}} \frac{20}{8} = 2.5$$

Subtract 0.5 (correction factor) = 2.0

Multiply by 0.3(dilution interval) = 0.60

Add the highest dilution step with 100% cpe in all wells $(10^{-4.9}) = 10^{-5.5}$ The virus titre is expressed as $10^{5.5}$ tcid50/ml The results from this study clearly show that the field isolate, from which the mutant virus was derived, is denatured considerably at a temperature of 50° C. whereas both the mutant virus shows only a slight reduction in virus titre. Sequence analyses of the mutant virus indicates a number of amino acid changes from that of the original field isolate (FIGS. 6, 7 and 8).

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in virology, molecular biology or related fields are intended to be within the scope of the following claims.

The invention claimed is:

1. A foot and mouth disease virus (FMDV) having improved stability compared to the field isolate of the same subtype, wherein the virus comprises at least the following mutations: VP2 A193S, VP2 LEK78-80SAR, VP2 S110T, VP2 T88A, VP2 E131K, VP3 H85P and VP3 E196A.

2. The FMDV according to claim 1 which is based on an FMDV A strain.

3. The FMDV according to claim 1, wherein the FMDV has improved thermostability compared to the field isolate of the same subtype.

4. A foot and mouth disease vaccine comprising an inactivated, dead, or attenuated FMDV according to claim 1.

5. A method of preventing foot and mouth disease in a subject which comprises the step of administrating a vaccine according to claim 4 to the subject.

6. A method of making a foot and mouth disease virus (FMDV) having improved stability compared to the field isolate of the same subtype comprising the step of introducing at least the mutations VP2 A193S, VP2 LEK78-80SAR, VP2 S110T, VP2 T88A, VP2 E131K, VP3 H85P and VP3 E196A into an FMDV field isolate or vaccine strain.

7. A method for improving the stability of an FMDV which comprises the step of introducing at least the mutations VP2 A193S, VP2 LEK78-80SAR, VP2 S110T, VP2 T88A, VP2 E131K, VP3 H85P and VP3 E196A.

* * * * *

SEQUENCE LISTING

```
<160> NUMBER OF SEQ ID NOS: 11

<210> SEQ ID NO 1
<211> LENGTH: 218
<212> TYPE: PRT
<213> ORGANISM: Foot-and-mouth disease virus

<400> SEQUENCE: 1
```

```
Asp Lys Lys Thr Glu Glu Thr Thr Leu Leu Glu Asp Arg Ile Leu Thr
 1               5                  10                  15

Thr Arg Asn Gly His Thr Ser Thr Thr Gln Ser Ser Val Gly Val
            20                  25                  30

Thr Tyr Gly Tyr Ser Thr Gly Glu Asp His Val Ser Gly Pro Asn Thr
            35                  40                  45

Ser Gly Leu Glu Thr Arg Val Val Gln Ala Glu Arg Phe Phe Lys Lys
 50                  55                  60

His Leu Phe Asp Trp Thr Pro Asp Lys Pro Phe Gly His Leu Glu Lys
 65                  70                  75                  80

Leu Glu Leu Pro Thr Glu His Thr Gly Val Tyr Gly His Leu Val Glu
                85                  90                  95

Ser Phe Ala Tyr Met Arg Asn Gly Trp Asp Val Glu Val Ser Ala Val
            100                 105                 110

Gly Asn Gln Phe Asn Gly Gly Cys Leu Leu Val Ala Met Val Pro Glu
            115                 120                 125

Trp Lys Glu Phe Thr Gln Arg Glu Lys Tyr Gln Leu Thr Leu Phe Pro
 130                 135                 140

His Gln Phe Ile Ser Pro Arg Thr Asn Met Thr Ala His Ile Thr Val
 145                 150                 155                 160

Pro Tyr Leu Gly Val Asn Arg Tyr Asp Gln Tyr Lys Lys His Lys Pro
            165                 170                 175

Trp Thr Leu Val Val Met Val Val Ser Pro Leu Thr Thr Ser Ser Ile
            180                 185                 190

Ala Ala Gly Gln Ile Lys Val Tyr Ala Asn Ile Ala Pro Thr His Val
            195                 200                 205

His Val Ala Gly Glu Leu Pro Ser Lys Glu
 210                 215

<210> SEQ ID NO 2
<211> LENGTH: 221
<212> TYPE: PRT
<213> ORGANISM: Foot-and-mouth disease virus

<400> SEQUENCE: 2

Gly Ile Val Pro Val Ala Cys Ser Asp Gly Tyr Gly Gly Leu Val Thr
 1               5                  10                  15

Thr Asp Pro Lys Thr Ala Asp Pro Val Tyr Gly Met Val Tyr Asn Pro
            20                  25                  30

Pro Arg Thr Asn Tyr Pro Gly Arg Phe Thr Asn Leu Leu Asp Val Ala
            35                  40                  45

Glu Ala Cys Pro Thr Leu Leu Cys Phe Glu Asn Gly Lys Pro Tyr Val
 50                  55                  60

Glu Thr Arg Thr Asp Asp Gln Arg Leu Leu Ala Lys Phe Asp Val Ser
 65                  70                  75                  80

Leu Ala Ala Lys His Met Ser Asn Thr Tyr Leu Ala Gly Ile Ala Gln
            85                  90                  95

Tyr Tyr Ala Gln Tyr Ser Gly Thr Ile Asn Leu His Phe Met Phe Thr
            100                 105                 110

Gly Ser Thr Asp Ser Lys Ala Arg Tyr Met Val Ala Tyr Val Pro Pro
            115                 120                 125

Gly Val Asp Thr Pro Pro Asp Ala Pro Glu Arg Ala Ala His Cys Ile
 130                 135                 140

His Ala Glu Trp Asp Thr Gly Leu Asn Ser Lys Phe Thr Phe Ser Ile
```

```
                145                 150                 155                 160
Pro Tyr Met Ser Ala Ala Asp Tyr Ala Tyr Thr Ala Ser Asp Val Ala
                    165                 170                 175

Glu Thr Thr Asn Val Gln Gly Trp Val Cys Ile Tyr Gln Ile Thr His
                180                 185                 190

Gly Lys Ala Glu Gln Asp Thr Leu Val Val Ser Val Ser Ala Gly Lys
                    195                 200                 205

Asp Phe Glu Leu Arg Leu Pro Ile Asp Pro Arg Ala Gln
                210                 215                 220

<210> SEQ ID NO 3
<211> LENGTH: 736
<212> TYPE: PRT
<213> ORGANISM: Foot-and-mouth disease virus

<400> SEQUENCE: 3

Gly Ala Gly Gln Ser Ser Pro Ala Thr Gly Ser Gln Asn Gln Ser Gly
1               5                   10                  15

Asn Thr Gly Ser Ile Ile Asn Asn Tyr Tyr Met Gln Gln Tyr Gln Asn
                20                  25                  30

Ser Met Asp Thr Gln Leu Gly Asp Asn Ala Ile Ser Gly Gly Ser Asn
            35                  40                  45

Glu Gly Ser Thr Asp Thr Thr Ser Thr His Thr Asn Asn Thr Gln Asn
        50                  55                  60

Asn Asp Trp Phe Ser Lys Leu Ala Ser Ser Ala Phe Thr Gly Leu Phe
65                  70                  75                  80

Gly Ala Leu Leu Ala Asp Lys Lys Thr Glu Glu Thr Thr Leu Leu Glu
                85                  90                  95

Asp Arg Ile Leu Thr Thr Arg Asn Gly His Thr Thr Ser Thr Thr Gln
                100                 105                 110

Ser Ser Val Gly Val Thr Tyr Gly Tyr Ser Thr Gly Glu Asp His Val
            115                 120                 125

Ser Gly Pro Asn Thr Ser Gly Leu Glu Thr Arg Val Val Gln Ala Glu
        130                 135                 140

Arg Phe Phe Lys Lys His Leu Phe Asp Trp Thr Pro Asp Lys Pro Phe
145                 150                 155                 160

Gly His Leu Glu Lys Leu Glu Leu Pro Thr Glu His Thr Gly Val Tyr
                165                 170                 175

Gly His Leu Val Glu Ser Phe Ala Tyr Met Arg Asn Gly Trp Asp Val
                180                 185                 190

Glu Val Ser Ala Val Gly Asn Gln Phe Asn Gly Gly Cys Leu Leu Val
            195                 200                 205

Ala Met Val Pro Glu Trp Lys Glu Phe Thr Gln Arg Glu Lys Tyr Gln
        210                 215                 220

Leu Thr Leu Phe Pro His Gln Phe Ile Ser Pro Arg Thr Asn Met Thr
225                 230                 235                 240

Ala His Ile Thr Val Pro Tyr Leu Gly Val Asn Arg Tyr Asp Gln Tyr
                245                 250                 255

Lys Lys His Lys Pro Trp Thr Leu Val Val Met Val Val Ser Pro Leu
                260                 265                 270

Thr Thr Ser Ser Ile Ala Ala Gly Gln Ile Lys Val Tyr Ala Asn Ile
            275                 280                 285

Ala Pro Thr His Val His Val Ala Gly Glu Leu Pro Ser Lys Glu Gly
        290                 295                 300
```

-continued

```
Ile Val Pro Val Ala Cys Ser Asp Gly Tyr Gly Leu Val Thr Thr
305                 310                 315                 320

Asp Pro Lys Thr Ala Asp Pro Val Tyr Gly Met Val Tyr Asn Pro Pro
            325                 330                 335

Arg Thr Asn Tyr Pro Gly Arg Phe Thr Asn Leu Leu Asp Val Ala Glu
        340                 345                 350

Ala Cys Pro Thr Leu Leu Cys Phe Glu Asn Gly Lys Pro Tyr Val Glu
    355                 360                 365

Thr Arg Thr Asp Asp Gln Arg Leu Leu Ala Lys Phe Asp Val Ser Leu
370                 375                 380

Ala Ala Lys His Met Ser Asn Thr Tyr Leu Ala Gly Ile Ala Gln Tyr
385                 390                 395                 400

Tyr Ala Gln Tyr Ser Gly Thr Ile Asn Leu His Phe Met Phe Thr Gly
            405                 410                 415

Ser Thr Asp Ser Lys Ala Arg Tyr Met Val Ala Tyr Val Pro Pro Gly
        420                 425                 430

Val Asp Thr Pro Pro Asp Ala Pro Glu Arg Ala Ala His Cys Ile His
    435                 440                 445

Ala Glu Trp Asp Thr Gly Leu Asn Ser Lys Phe Thr Phe Ser Ile Pro
450                 455                 460

Tyr Met Ser Ala Ala Asp Tyr Ala Tyr Thr Ala Ser Asp Val Ala Glu
465                 470                 475                 480

Thr Thr Asn Val Gln Gly Trp Val Cys Ile Tyr Gln Ile Thr His Gly
            485                 490                 495

Lys Ala Glu Gln Asp Thr Leu Val Val Ser Val Ser Ala Gly Lys Asp
        500                 505                 510

Phe Glu Leu Arg Leu Pro Ile Asp Pro Arg Ala Gln Thr Thr Ala Thr
    515                 520                 525

Gly Glu Ser Ala Asp Pro Val Thr Thr Val Glu Asn Tyr Gly Gly
530                 535                 540

Glu Thr Gln Val Arg Arg Gln His Thr Asp Val Ser Phe Ile Met
545                 550                 555                 560

Asp Arg Phe Val Lys Ile Asn Pro Val Thr Pro Thr His Val Ile Asp
            565                 570                 575

Leu Met Gln Thr His Gln His Ala Leu Val Gly Ala Leu Leu Arg Ala
        580                 585                 590

Ala Thr Tyr Tyr Phe Ser Asp Leu Glu Ile Val Val Arg His Glu Gly
    595                 600                 605

Asn Leu Thr Trp Val Pro Asn Gly Ala Pro Glu Ala Ala Leu Ser Asn
610                 615                 620

Thr Ser Asn Pro Thr Ala Tyr His Lys Glu Pro Phe Thr Arg Leu Ala
625                 630                 635                 640

Leu Pro Tyr Thr Ala Pro His Arg Val Leu Ala Thr Val Tyr Asn Gly
            645                 650                 655

Thr Asn Lys Tyr Ala Ala Thr Gly Ala Arg Arg Gly Asp Leu Gly Ser
        660                 665                 670

Leu Ala Ala Arg Val Ala Ala Gln Leu Pro Ser Ser Phe Asn Phe Gly
    675                 680                 685

Ala Ile Arg Ala Thr Thr Ile His Glu Leu Leu Val Arg Met Arg Arg
690                 695                 700

Ala Glu Leu Tyr Cys Pro Arg Pro Leu Leu Ala Met Glu Val Ser Ala
705                 710                 715                 720

Glu Gly Arg His Lys Gln Lys Ile Ile Ala Pro Ala Lys Gln Leu Leu
```

725                 730                 735

<210> SEQ ID NO 4
<211> LENGTH: 734
<212> TYPE: PRT
<213> ORGANISM: Foot-and-mouth disease virus

<400> SEQUENCE: 4

Gly Ala Gly Gln Ser Ser Pro Ala Thr Gly Ser Gln Asn Gln Ser Gly
1               5                   10                  15

Asn Thr Gly Ser Ile Ile Asn Asn Tyr Tyr Met Gln Gln Tyr Gln Asn
            20                  25                  30

Ser Met Asp Thr Gln Leu Gly Asp Asn Ala Ile Ser Gly Gly Ser Asn
        35                  40                  45

Glu Gly Ser Thr Asp Thr Thr Ser Thr His Thr Asn Asn Thr Gln Asn
    50                  55                  60

Asn Asp Trp Phe Ser Lys Leu Ala Ser Ser Ala Phe Thr Gly Leu Phe
65                  70                  75                  80

Gly Ala Leu Leu Ala Asp Lys Lys Thr Glu Glu Thr Thr Leu Leu Glu
                85                  90                  95

Asp Arg Ile Leu Thr Thr Arg Asn Gly His Thr Thr Ser Thr Thr Gln
            100                 105                 110

Ser Ser Val Gly Val Thr Tyr Gly Tyr Ser Thr Gly Glu Asp His Val
        115                 120                 125

Ser Gly Pro Asn Thr Ser Gly Leu Glu Thr Arg Val Val Gln Ala Glu
    130                 135                 140

Arg Phe Phe Lys Lys His Leu Phe Asp Trp Thr Pro Asp Lys Pro Phe
145                 150                 155                 160

Gly His Leu Glu Lys Leu Glu Leu Pro Thr Glu His Thr Gly Val Tyr
                165                 170                 175

Gly His Leu Val Glu Ser Phe Ala Tyr Met Arg Asn Gly Trp Asp Val
            180                 185                 190

Glu Val Ser Ala Val Gly Asn Gln Phe Asn Gly Gly Cys Leu Leu Val
        195                 200                 205

Ala Met Val Pro Glu Trp Lys Glu Phe Thr Gln Arg Glu Lys Tyr Gln
    210                 215                 220

Leu Thr Leu Phe Pro His Gln Phe Ile Ser Pro Arg Thr Asn Met Thr
225                 230                 235                 240

Ala His Ile Thr Val Pro Tyr Leu Gly Val Asn Arg Tyr Asp Gln Tyr
                245                 250                 255

Lys Lys His Lys Pro Trp Thr Leu Val Val Met Val Val Ser Pro Leu
            260                 265                 270

Thr Thr Ser Ser Ile Ala Ala Gly Gln Ile Lys Val Tyr Ala Asn Ile
        275                 280                 285

Ala Pro Thr His Val His Val Ala Gly Glu Leu Pro Ser Lys Glu Gly
    290                 295                 300

Ile Val Pro Val Ala Cys Ser Asp Gly Tyr Gly Gly Leu Val Thr Thr
305                 310                 315                 320

Asp Pro Lys Thr Ala Asp Pro Val Tyr Gly Met Val Tyr Asn Pro Pro
                325                 330                 335

Arg Thr Asn Tyr Pro Gly Arg Phe Thr Asn Leu Leu Asp Val Ala Glu
            340                 345                 350

Ala Cys Pro Thr Leu Leu Cys Phe Glu Asn Gly Lys Pro Tyr Val Glu
        355                 360                 365

```
Thr Arg Thr Asp Asp Gln Arg Leu Leu Ala Lys Phe Asp Val Ser Leu
    370                 375                 380

Ala Ala Lys His Met Ser Asn Thr Tyr Leu Ala Gly Ile Ala Gln Tyr
385                 390                 395                 400

Tyr Ala Gln Tyr Ser Gly Thr Ile Asn Leu His Phe Met Phe Thr Gly
                405                 410                 415

Ser Thr Asp Ser Lys Ala Arg Tyr Met Val Ala Tyr Val Pro Pro Gly
                420                 425                 430

Val Asp Thr Pro Pro Asp Ala Pro Glu Arg Ala Ala His Cys Ile His
            435                 440                 445

Ala Glu Trp Asp Thr Gly Leu Asn Ser Lys Thr Phe Ser Ile Pro
450                 455                 460

Tyr Met Ser Ala Ala Asp Tyr Ala Tyr Thr Ala Ser Asp Val Ala Glu
465                 470                 475                 480

Thr Thr Asn Val Gln Gly Trp Val Cys Ile Tyr Gln Ile Thr His Gly
                485                 490                 495

Lys Ala Glu Gln Asp Thr Leu Val Val Ser Val Ser Ala Gly Lys Asp
                500                 505                 510

Phe Glu Leu Arg Leu Pro Ile Asp Pro Arg Ala Gln Thr Thr Ala Thr
            515                 520                 525

Gly Glu Ser Ala Asp Pro Val Thr Thr Thr Val Glu Asn Tyr Gly Gly
530                 535                 540

Glu Thr Gln Val Arg Arg Arg Gln His Thr Asp Val Ser Phe Ile Met
545                 550                 555                 560

Asp Arg Phe Val Lys Ile Asn Pro Val Thr Pro Thr His Val Ile Asp
                565                 570                 575

Leu Met Gln Thr His Gln His Ala Leu Val Gly Ala Leu Leu Arg Ala
                580                 585                 590

Ala Thr Tyr Tyr Phe Ser Asp Leu Glu Ile Val Val Arg His Glu Gly
            595                 600                 605

Asn Leu Thr Trp Val Pro Asn Gly Ala Pro Glu Ala Ala Leu Ser Asn
610                 615                 620

Thr Ser Asn Pro Thr Ala Tyr His Lys Glu Pro Phe Thr Arg Leu Ala
625                 630                 635                 640

Leu Pro Tyr Thr Ala Pro His Arg Val Leu Ala Thr Val Tyr Asn Gly
                645                 650                 655

Thr Asn Lys Tyr Ala Ala Thr Gly Ala Arg Arg Gly Asp Leu Gly Ser
                660                 665                 670

Leu Ala Ala Arg Val Ala Ala Gln Leu Pro Ser Ser Phe Asn Phe Gly
            675                 680                 685

Ala Ile Arg Ala Thr Thr Ile His Glu Leu Leu Val Arg Met Arg Arg
690                 695                 700

Ala Glu Leu Tyr Cys Pro Arg Pro Leu Leu Ala Met Glu Val Ser Ala
705                 710                 715                 720

Glu Gly Arg His Lys Gln Lys Ile Ile Ala Pro Ala Lys Gln
                725                 730

<210> SEQ ID NO 5
<211> LENGTH: 734
<212> TYPE: PRT
<213> ORGANISM: Foot-and-mouth disease virus

<400> SEQUENCE: 5

Gly Ala Gly Gln Ser Ser Pro Ala Thr Gly Ser Gln Asn Gln Ser Gly
1               5                   10                  15
```

-continued

```
Asn Thr Gly Ser Ile Ile Asn Asn Tyr Tyr Met Gln Gln Tyr Gln Asn
             20                  25                  30

Ser Met Asp Thr Gln Leu Gly Asp Asn Ala Ile Ser Gly Gly Ser Asn
         35                  40                  45

Glu Gly Ser Thr Asp Thr Thr Ser Thr His Thr Asn Asn Thr Gln Asn
 50                  55                  60

Asn Asp Trp Phe Ser Lys Leu Ala Ser Ser Ala Phe Thr Gly Leu Phe
 65                  70                  75                  80

Gly Ala Leu Leu Ala Asp Lys Lys Thr Glu Glu Thr Thr Leu Leu Glu
                 85                  90                  95

Asp Arg Ile Leu Thr Thr Arg Asn Gly His Thr Thr Ser Thr Thr Gln
             100                 105                 110

Ser Ser Val Gly Val Thr Tyr Gly Tyr Ser Thr Gly Glu Asp His Val
         115                 120                 125

Ser Gly Pro Asn Thr Ser Gly Leu Glu Thr Arg Val Val Gln Ala Glu
130                 135                 140

Arg Phe Phe Lys Lys His Leu Phe Asp Trp Thr Pro Asp Lys Pro Phe
145                 150                 155                 160

Gly His Ser Ala Arg Leu Glu Leu Pro Thr Glu His Ala Gly Val Tyr
                 165                 170                 175

Gly His Leu Val Glu Ser Phe Ala Tyr Met Arg Asn Gly Trp Asp Val
             180                 185                 190

Glu Val Thr Ala Val Gly Asn Gln Phe Asn Gly Gly Cys Leu Leu Val
         195                 200                 205

Ala Met Val Pro Glu Trp Lys Lys Phe Thr Gln Arg Glu Lys Tyr Gln
210                 215                 220

Leu Thr Leu Phe Pro His Gln Phe Ile Ser Pro Arg Thr Asn Met Thr
225                 230                 235                 240

Ala His Ile Thr Val Pro Tyr Leu Gly Val Asn Arg Tyr Asp Gln Tyr
                 245                 250                 255

Lys Lys His Lys Pro Trp Thr Leu Val Val Met Val Val Ser Pro Leu
             260                 265                 270

Thr Thr Ser Ser Ile Ser Ala Gly Gln Ile Lys Val Tyr Ala Asn Ile
         275                 280                 285

Ala Pro Thr His Val His Val Ala Gly Glu Leu Pro Ser Lys Glu Gly
290                 295                 300

Ile Val Pro Val Ala Cys Ser Asp Gly Tyr Gly Gly Leu Val Thr Thr
305                 310                 315                 320

Asp Pro Lys Thr Ala Asp Pro Val Tyr Gly Met Val Tyr Asn Pro Pro
                 325                 330                 335

Arg Thr Asn Tyr Pro Gly Arg Phe Thr Asn Leu Leu Asp Val Ala Glu
             340                 345                 350

Ala Cys Pro Thr Leu Leu Cys Phe Glu Asn Gly Lys Pro Tyr Val Glu
         355                 360                 365

Thr Arg Thr Asp Asp Gln Arg Leu Leu Ala Lys Phe Asp Val Ser Leu
370                 375                 380

Ala Ala Lys Pro Met Ser Asn Thr Tyr Leu Ala Gly Ile Ala Gln Tyr
385                 390                 395                 400

Tyr Ala Gln Tyr Ser Gly Thr Ile Asn Leu His Phe Met Phe Thr Gly
                 405                 410                 415

Ser Thr Asp Ser Lys Ala Arg Tyr Met Val Ala Tyr Val Pro Pro Gly
             420                 425                 430
```

```
Val Asp Thr Pro Pro Asp Ala Pro Glu Arg Ala Ala His Cys Ile His
            435                 440                 445

Ala Glu Trp Asp Thr Gly Leu Asn Ser Lys Phe Thr Phe Ser Ile Pro
450                 455                 460

Tyr Met Ser Ala Ala Asp Tyr Ala Tyr Thr Ala Ser Asp Val Ala Glu
465                 470                 475                 480

Thr Thr Asn Val Gln Gly Trp Val Cys Ile Tyr Gln Ile Thr His Gly
                485                 490                 495

Lys Ala Ala Gln Asp Thr Leu Val Val Ser Val Ser Ala Gly Lys Asp
                500                 505                 510

Phe Glu Leu Arg Leu Pro Ile Asp Pro Arg Ala Gln Thr Thr Ala Thr
                515                 520                 525

Gly Glu Ser Ala Asp Pro Val Thr Thr Thr Val Glu Asn Tyr Gly Gly
            530                 535                 540

Glu Thr Gln Val Arg Arg Arg Gln His Thr Asp Val Ser Phe Ile Met
545                 550                 555                 560

Asp Arg Phe Val Lys Ile Asn Pro Val Thr Pro Thr His Val Ile Asp
                565                 570                 575

Leu Met Gln Thr His Gln His Ala Leu Val Gly Ala Leu Leu Arg Ala
                580                 585                 590

Ala Thr Tyr Tyr Phe Ser Asp Leu Glu Ile Val Val Arg His Glu Gly
            595                 600                 605

Asn Leu Thr Trp Val Pro Asn Gly Ala Pro Glu Ala Ala Leu Ser Asn
            610                 615                 620

Thr Ser Asn Pro Thr Ala Tyr His Lys Glu Pro Phe Thr Arg Leu Ala
625                 630                 635                 640

Leu Pro Tyr Thr Ala Pro His Arg Val Leu Ala Thr Val Tyr Asn Gly
                645                 650                 655

Thr Asn Lys Tyr Ala Ala Thr Gly Asp Ser Arg Gly Asp Leu Gly Pro
                660                 665                 670

Leu Ala Ala Arg Val Ala Ala Gln Leu Pro Ser Ser Phe Asn Phe Gly
                675                 680                 685

Ala Ile Arg Ala Thr Thr Ile His Glu Leu Leu Val Arg Met Arg Arg
            690                 695                 700

Ala Glu Leu Tyr Cys Pro Arg Pro Leu Leu Ala Met Glu Val Ser Ala
705                 710                 715                 720

Glu Gly Arg His Lys Gln Lys Ile Ile Ala Pro Ala Lys Gln
                725                 730

<210> SEQ ID NO 6
<211> LENGTH: 734
<212> TYPE: PRT
<213> ORGANISM: Foot-and-mouth disease virus

<400> SEQUENCE: 6

Gly Ala Gly Gln Ser Ser Pro Ala Thr Gly Ser Gln Asn Gln Ser Gly
1               5                   10                  15

Asn Thr Gly Ser Ile Ile Asn Asn Tyr Tyr Met Gln Gln Tyr Gln Asn
                20                  25                  30

Ser Met Asp Thr Gln Leu Gly Asp Asn Ala Ile Ser Gly Gly Ser Asn
            35                  40                  45

Glu Gly Ser Thr Asp Thr Thr Ser Thr His Thr Thr Asn Thr Gln Asn
        50                  55                  60

Asn Asp Trp Phe Ser Lys Leu Ala Ser Ser Ala Phe Ser Gly Leu Phe
65                  70                  75                  80
```

```
Gly Ala Leu Leu Ala Asp Lys Lys Thr Glu Glu Thr Leu Leu Glu
                     85                  90                  95

Asp Arg Ile Leu Thr Thr Arg Asn Gly His Thr Thr Ser Thr Thr Gln
            100                 105                 110

Ser Ser Val Gly Val Thr Tyr Gly Tyr Ala Thr Ala Glu Asp Phe Val
            115                 120                 125

Ser Gly Pro Asn Thr Ser Gly Leu Glu Thr Arg Val Val Gln Ala Glu
130                 135                 140

Arg Phe Phe Lys Thr His Leu Phe Asp Trp Val Thr Ser Asp Ser Phe
145                 150                 155                 160

Gly Arg Tyr His Leu Leu Glu Leu Pro Thr Asp His Lys Gly Val Tyr
                165                 170                 175

Gly Ser Leu Thr Asp Ser Tyr Ala Tyr Met Arg Asn Gly Trp Asp Val
            180                 185                 190

Glu Val Thr Ala Val Gly Asn Gln Phe Asn Gly Gly Cys Leu Leu Val
            195                 200                 205

Ala Met Val Pro Glu Leu Cys Ser Ile Gln Lys Arg Glu Leu Tyr Gln
210                 215                 220

Leu Thr Leu Phe Pro His Gln Phe Ile Asn Pro Arg Thr Asn Met Thr
225                 230                 235                 240

Ala His Ile Thr Val Pro Phe Val Gly Val Asn Arg Tyr Asp Gln Tyr
                245                 250                 255

Lys Val His Lys Pro Trp Thr Leu Val Val Met Val Val Ala Pro Leu
            260                 265                 270

Thr Val Asn Thr Glu Gly Ala Pro Gln Ile Lys Val Tyr Ala Asn Ile
            275                 280                 285

Ala Pro Thr Asn Val His Val Ala Gly Glu Phe Pro Ser Lys Glu Gly
290                 295                 300

Ile Phe Pro Val Ala Cys Ser Asp Gly Tyr Gly Gly Leu Val Thr Thr
305                 310                 315                 320

Asp Pro Lys Thr Ala Asp Pro Val Tyr Gly Lys Val Phe Asn Pro Pro
                325                 330                 335

Arg Asn Gln Leu Pro Gly Arg Phe Thr Asn Leu Leu Asp Val Ala Glu
            340                 345                 350

Ala Cys Pro Thr Phe Leu His Phe Glu Gly Asp Val Pro Tyr Val Thr
            355                 360                 365

Thr Lys Thr Asp Ser Asp Arg Val Leu Ala Gln Phe Asp Met Ser Leu
370                 375                 380

Ala Ala Lys His Met Ser Asn Thr Phe Leu Ala Gly Leu Ala Gln Tyr
385                 390                 395                 400

Tyr Thr Gln Tyr Ser Gly Thr Ile Asn Leu His Phe Met Phe Thr Gly
                405                 410                 415

Pro Thr Asp Ala Lys Ala Arg Tyr Met Ile Ala Tyr Ala Pro Pro Gly
            420                 425                 430

Met Glu Pro Pro Lys Thr Pro Glu Ala Ala His Cys Ile His Ala
            435                 440                 445

Glu Trp Asp Thr Gly Leu Asn Ser Lys Phe Thr Phe Ser Ile Pro Tyr
450                 455                 460

Leu Ser Ala Ala Asp Tyr Ala Tyr Thr Ala Ser Asp Val Ala Glu Thr
465                 470                 475                 480

Thr Asn Val Gln Gly Trp Val Cys Leu Phe Gln Ile Thr His Gly Lys
                485                 490                 495
```

```
Ala Asp Gly Asp Ala Leu Val Val Leu Ala Ser Ala Gly Lys Asp Phe
            500                 505                 510

Glu Leu Arg Leu Pro Val Asp Ala Arg Ala Glu Thr Thr Ser Ala Gly
        515                 520                 525

Glu Ser Ala Asp Pro Val Thr Thr Thr Val Glu Asn Tyr Gly Gly Glu
    530                 535                 540

Thr Gln Ile Gln Arg Arg Gln His Thr Asp Val Ser Phe Ile Met Asp
545                 550                 555                 560

Arg Phe Val Lys Val Thr Pro Gln Asn Gln Ile Asn Ile Leu Asp Leu
                565                 570                 575

Met Gln Val Pro Ser His Thr Leu Val Gly Ala Leu Leu Arg Ala Ser
            580                 585                 590

Thr Tyr Tyr Phe Ser Asp Leu Glu Ile Ala Val Lys His Glu Gly Asp
        595                 600                 605

Leu Thr Trp Val Pro Asn Gly Ala Pro Glu Lys Ala Leu Asp Asn Thr
    610                 615                 620

Thr Asn Pro Thr Ala Tyr His Lys Ala Pro Leu Thr Arg Leu Ala Leu
625                 630                 635                 640

Pro Tyr Thr Ala Pro His Arg Val Leu Ala Thr Val Tyr Asn Gly Glu
                645                 650                 655

Cys Arg Tyr Ser Arg Asn Ala Val Pro Asn Leu Arg Gly Asp Leu Gln
            660                 665                 670

Val Leu Ala Gln Lys Val Ala Arg Thr Leu Pro Thr Ser Phe Asn Tyr
        675                 680                 685

Gly Ala Ile Lys Ala Thr Arg Val Thr Glu Leu Leu Tyr Arg Met Lys
    690                 695                 700

Arg Ala Glu Thr Tyr Cys Pro Arg Pro Leu Leu Ala Ile His Pro Thr
705                 710                 715                 720

Glu Ala Arg His Lys Gln Lys Ile Val Ala Pro Val Lys Gln
                725                 730

<210> SEQ ID NO 7
<211> LENGTH: 731
<212> TYPE: PRT
<213> ORGANISM: Foot-and-mouth disease virus

<400> SEQUENCE: 7

Gly Ala Gly Gln Ser Ser Pro Ala Thr Gly Ser Gln Asn Gln Ser Gly
1               5                   10                  15

Asn Thr Gly Ser Ile Ile Asn Asn Tyr Tyr Met Gln Gln Tyr Gln Asn
            20                  25                  30

Ser Met Asp Thr Gln Leu Gly Asp Asn Ala Ile Ser Gly Gly Ser Asn
        35                  40                  45

Glu Gly Ser Thr Asp Thr Thr Ser Thr His Thr Thr Asn Thr Gln Asn
    50                  55                  60

Asn Asp Trp Phe Ser Lys Leu Ala Ser Ser Ala Phe Ser Gly Leu Phe
65                  70                  75                  80

Gly Ala Leu Leu Ala Asp Lys Lys Thr Glu Glu Thr Thr Leu Leu Glu
                85                  90                  95

Asp Arg Ile Leu Thr Thr Arg Asn Gly His Thr Thr Ser Thr Thr Gln
            100                 105                 110

Ser Ser Val Gly Val Thr Tyr Gly Tyr Ala Thr Ala Glu Asp Ser Ser
        115                 120                 125

Ser Gly Pro Asn Thr Ser Gly Leu Glu Thr Arg Val His Gln Ala Glu
    130                 135                 140
```

-continued

```
Arg Phe Phe Lys Met Thr Leu Phe Asp Trp Val Pro Ser Gln Asn Phe
145                 150                 155                 160

Gly His Met His Lys Val Val Leu Pro Thr Asp Pro Lys Gly Val Tyr
                165                 170                 175

Gly Gly Leu Val Lys Ser Tyr Ala Tyr Met Arg Asn Gly Trp Asp Val
            180                 185                 190

Glu Val Thr Ala Val Gly Asn Gln Phe Asn Gly Gly Cys Leu Leu Val
        195                 200                 205

Ala Leu Val Pro Glu Met Gly Asp Ile Ser Asp Arg Glu Lys Tyr Gln
    210                 215                 220

Leu Thr Leu Tyr Pro His Gln Phe Ile Asn Pro Arg Thr Asn Met Thr
225                 230                 235                 240

Ala His Ile Thr Val Pro Tyr Val Gly Val Asn Arg Tyr Asp Gln Tyr
                245                 250                 255

Lys Gln His Lys Pro Trp Thr Leu Val Val Met Val Val Ala Pro Leu
                260                 265                 270

Thr Val Asn Thr Ser Gly Ala Gln Gln Ile Lys Val Tyr Ala Asn Ile
            275                 280                 285

Ala Pro Thr Asn Val His Val Ala Gly Glu Leu Pro Ser Lys Glu Gly
        290                 295                 300

Ile Phe Pro Val Ala Cys Ala Asp Gly Tyr Gly Asn Met Val Thr Thr
305                 310                 315                 320

Asp Pro Lys Thr Ala Asp Pro Ala Tyr Gly Lys Val Tyr Asn Pro Pro
                325                 330                 335

Arg Thr Ala Leu Pro Gly Arg Phe Thr Asn Tyr Leu Asp Val Ala Glu
            340                 345                 350

Ala Cys Pro Thr Phe Leu Val Phe Glu Asn Val Pro Tyr Val Ser Thr
        355                 360                 365

Arg Thr Asp Gly Gln Arg Leu Leu Ala Lys Phe Asp Val Ser Leu Ala
370                 375                 380

Ala Arg His Met Ser Asn Thr Tyr Leu Ala Gly Leu Ala Gln Tyr Tyr
385                 390                 395                 400

Thr Gln Tyr Ala Gly Thr Ile Asn Leu His Phe Met Phe Thr Gly Pro
                405                 410                 415

Thr Asp Ala Lys Ala Arg Tyr Met Val Ala Tyr Val Pro Pro Gly Met
            420                 425                 430

Glu Ala Pro Glu Asn Pro Glu Glu Ala Ala His Cys Ile His Ala Glu
        435                 440                 445

Trp Asp Thr Gly Leu Asn Ser Lys Phe Thr Phe Ser Ile Pro Tyr Ile
450                 455                 460

Ser Ala Ala Asp Tyr Ala Tyr Thr Ala Ser Asn Glu Ala Glu Thr Thr
465                 470                 475                 480

Cys Val Gln Gly Trp Val Cys Val Tyr Gln Ile Thr His Gly Lys Ala
                485                 490                 495

Asp Ala Asp Ala Leu Val Ile Ser Ala Ser Ala Gly Lys Asp Phe Glu
            500                 505                 510

Leu Arg Leu Pro Val Asp Ala Arg Gln Gln Thr Thr Thr Thr Gly Glu
        515                 520                 525

Ser Ala Asp Pro Val Thr Thr Thr Val Glu Asn Tyr Gly Gly Glu Thr
    530                 535                 540

Gln Val Gln Arg Arg His His Thr Asp Val Ala Phe Val Leu Asp Arg
545                 550                 555                 560
```

```
Phe Val Lys Val Pro Val Ser Asp Arg Gln Gln His Thr Leu Asp Val
                565                 570                 575
Met Gln Val His Lys Asp Ser Ile Val Gly Ala Leu Leu Arg Ala Ala
            580                 585                 590
Thr Tyr Tyr Phe Ser Asp Leu Glu Ile Ala Val Thr His Thr Gly Lys
        595                 600                 605
Leu Thr Trp Val Pro Asn Gly Ala Pro Val Ser Ala Leu Asp Asn Thr
    610                 615                 620
Thr Asn Pro Thr Ala Tyr His Lys Gly Pro Leu Thr Arg Leu Ala Leu
625                 630                 635                 640
Pro Tyr Thr Ala Pro His Arg Val Leu Ala Thr Thr Tyr Thr Gly Thr
                645                 650                 655
Thr Thr Tyr Thr Thr Ser Ala Arg Arg Gly Asp Ser Ala His Leu Ala
            660                 665                 670
Ala Ala His Ala Arg His Leu Pro Thr Ser Phe Asn Phe Gly Ala Val
        675                 680                 685
Lys Ala Glu Thr Val Thr Glu Leu Leu Val Arg Met Lys Arg Ala Glu
    690                 695                 700
Leu Tyr Cys Pro Arg Pro Ile Leu Pro Ile Gln Pro Thr Gly Asp Arg
705                 710                 715                 720
His Lys Gln Pro Leu Ile Ala Pro Ala Lys Gln
                725                 730

<210> SEQ ID NO 8
<211> LENGTH: 730
<212> TYPE: PRT
<213> ORGANISM: Foot-and-mouth disease virus

<400> SEQUENCE: 8

Gly Ala Gly Gln Ser Ser Pro Ala Thr Gly Ser Gln Asn Gln Ser Gly
1               5                   10                  15
Asn Thr Gly Ser Ile Ile Asn Asn Tyr Tyr Met Gln Gln Tyr Gln Asn
            20                  25                  30
Ser Met Asp Thr Gln Leu Gly Asp Asn Ala Ile Ser Gly Gly Ser Asn
        35                  40                  45
Glu Gly Ser Thr Asp Thr Thr Ser Thr His Thr Thr Asn Thr Gln Asn
    50                  55                  60
Asn Asp Trp Phe Ser Arg Leu Ala Ser Ser Ala Phe Ser Gly Leu Phe
65                  70                  75                  80
Gly Ala Leu Leu Ala Asp Lys Lys Thr Glu Glu Thr Thr Leu Leu Glu
                85                  90                  95
Asp Arg Ile Leu Thr Thr Arg Asn Gly His Thr Thr Ser Thr Thr Gln
            100                 105                 110
Ser Ser Val Gly Val Thr Tyr Gly Tyr Ala Val Thr Glu Asp Ala Val
        115                 120                 125
Ser Gly Pro Asn Thr Ser Gly Leu Glu Thr Arg Val Thr Gln Ala Glu
    130                 135                 140
Arg Phe Phe Lys Lys His Leu Phe Asp Trp Thr Pro Asn Leu Ala Phe
145                 150                 155                 160
Gly His Cys His Tyr Leu Glu Leu Pro Thr Glu His Lys Gly Val Tyr
                165                 170                 175
Gly Ser Leu Met Asp Ser Tyr Ala Tyr Met Arg Asn Gly Trp Asp Ile
            180                 185                 190
Glu Val Thr Ala Val Gly Asn Gln Phe Asn Gly Gly Cys Leu Leu Val
        195                 200                 205
```

```
Ala Leu Val Pro Glu Leu Lys Glu Leu Asp Thr Arg Gln Lys Tyr Gln
        210                 215                 220

Leu Thr Leu Phe Pro His Gln Phe Ile Asn Pro Arg Thr Asn Met Thr
225                 230                 235                 240

Ala His Ile Asn Val Pro Phe Val Gly Val Asn Arg Tyr Asp Gln Tyr
                245                 250                 255

Ala Leu His Lys Pro Trp Thr Leu Val Val Met Val Ala Pro Leu
            260                 265                 270

Thr Val Lys Thr Gly Gly Ser Glu Gln Ile Lys Val Tyr Met Asn Ala
            275                 280                 285

Ala Pro Thr Tyr Val His Val Ala Gly Glu Leu Pro Ser Lys Glu Gly
        290                 295                 300

Ile Val Pro Val Ala Cys Ala Asp Gly Tyr Gly Asn Met Val Thr Thr
305                 310                 315                 320

Asp Pro Lys Thr Ala Asp Pro Val Tyr Gly Lys Val Phe Asn Pro Pro
                325                 330                 335

Arg Thr Asn Leu Pro Gly Arg Phe Thr Asn Phe Leu Asp Val Ala Glu
                340                 345                 350

Ala Cys Pro Thr Phe Leu Arg Phe Gly Glu Val Pro Phe Val Lys Thr
        355                 360                 365

Val Asn Ser Gly Asp Arg Leu Leu Ala Lys Phe Asp Val Ser Leu Ala
370                 375                 380

Ala Gly His Met Ser Asn Thr Tyr Leu Ala Gly Leu Ala Gln Tyr Tyr
385                 390                 395                 400

Thr Gln Tyr Ser Gly Thr Met Asn Ile His Phe Met Phe Thr Gly Pro
                405                 410                 415

Thr Asp Ala Lys Ala Arg Tyr Met Val Ala Tyr Val Pro Pro Gly Met
                420                 425                 430

Thr Pro Pro Thr Asp Pro Glu Arg Ala Ala His Cys Ile His Ser Glu
            435                 440                 445

Trp Asp Thr Gly Leu Asn Ser Lys Phe Thr Phe Ser Ile Pro Tyr Leu
450                 455                 460

Ser Ala Ala Asp Tyr Ala Tyr Thr Ala Ser Asp Val Ala Glu Ala Thr
465                 470                 475                 480

Ser Val Gln Gly Trp Val Cys Ile Tyr Gln Ile Thr His Gly Lys Ala
                485                 490                 495

Glu Gly Asp Ala Leu Val Val Ser Ala Ser Ala Gly Lys Asp Phe Glu
                500                 505                 510

Phe Arg Leu Pro Val Asp Ala Arg Gln Gln Thr Thr Thr Thr Gly Glu
            515                 520                 525

Ser Ala Asp Pro Val Thr Thr Thr Val Glu Asn Tyr Gly Gly Glu Thr
530                 535                 540

Gln Thr Ala Arg Arg Leu His Thr Asp Val Ala Phe Val Leu Asp Arg
545                 550                 555                 560

Phe Val Lys Phe Thr Pro Lys Asn Thr Gln Thr Leu Asp Leu Met Gln
                565                 570                 575

Ile Pro Ser His Thr Leu Val Gly Ala Leu Leu Arg Ser Ala Thr Tyr
            580                 585                 590

Tyr Phe Ser Asp Leu Glu Ile Ala Leu Val His Thr Gly Pro Val Thr
            595                 600                 605

Trp Val Pro Asn Gly Ala Pro Lys Thr Ala Leu Asp Asn Gln Thr Asn
610                 615                 620
```

```
Pro Thr Ala Tyr His Lys Gln Pro Ile Thr Arg Leu Ala Leu Pro Tyr
625                 630                 635                 640

Thr Ala Pro His Arg Val Leu Ala Thr Val Tyr Asn Gly Lys Thr Thr
        645                 650                 655

Tyr Gly Glu Glu Pro Thr Met Arg Gly Asp Arg Ala Val Leu Ala Ser
            660                 665                 670

Lys Val Asn Lys Gln Leu Pro Thr Ser Phe Asn Tyr Gly Ala Val Lys
                675                 680                 685

Ala Glu Asn Ile Thr Glu Met Leu Ile Arg Ile Lys Arg Ala Glu Thr
                690                 695                 700

Tyr Cys Pro Arg Pro Leu Leu Ala Leu Asp Thr Thr Gln Asp Arg Arg
705                 710                 715                 720

Lys Gln Glu Ile Ile Ala Pro Glu Lys Gln
                725                 730

<210> SEQ ID NO 9
<211> LENGTH: 744
<212> TYPE: PRT
<213> ORGANISM: Foot-and-mouth disease virus

<400> SEQUENCE: 9

Gly Ala Gly Gln Ser Ser Pro Ala Thr Gly Ser Gln Asn Gln Ser Gly
1               5                   10                  15

Asn Thr Gly Ser Ile Ile Asn Asn Tyr Tyr Met Gln Gln Tyr Gln Asn
                20                  25                  30

Ser Met Asp Thr Gln Leu Gly Asp Asn Ala Ile Ser Gly Gly Ser Asn
            35                  40                  45

Glu Gly Ser Thr Asp Thr Thr Ser Thr His Thr Asn Asn Thr Gln Asn
50                  55                  60

Asn Asp Trp Phe Ser Lys Leu Ala Gln Ser Ala Phe Ser Gly Leu Val
65                  70                  75                  80

Gly Ala Leu Leu Ala Asp Lys Lys Thr Glu Glu Thr Thr Leu Leu Glu
                85                  90                  95

Asp Arg Ile Val Thr Thr Ser His Gly Thr Thr Thr Ser Thr Thr Gln
            100                 105                 110

Ser Ser Val Gly Val Thr Tyr Gly Tyr Ala Leu Thr Asp Lys Phe Leu
        115                 120                 125

Pro Gly Pro Asn Thr Asn Gly Leu Glu Thr Arg Val Glu Gln Ala Glu
    130                 135                 140

Arg Phe Phe Lys His Lys Leu Phe Asp Trp Thr Leu Asp Gln Gln Phe
145                 150                 155                 160

Gly Thr Thr Tyr Val Leu Glu Leu Pro Thr Asp His Lys Gly Ile Tyr
                165                 170                 175

Gly Gln Leu Val Asp Ser His Ala Tyr Ile Arg Asn Gly Trp Asp Val
            180                 185                 190

Gln Val Ser Ala Thr Ala Thr Gln Phe Asn Gly Gly Cys Leu Leu Val
        195                 200                 205

Ala Met Val Pro Glu Leu Cys Lys Leu Asp Asp Arg Glu Lys Tyr Gln
    210                 215                 220

Leu Thr Leu Phe Pro His Gln Phe Leu Asn Pro Arg Thr Asn Thr Thr
225                 230                 235                 240

Ala His Ile Gln Val Pro Tyr Leu Gly Val Asp Arg His Asp Gln Gly
                245                 250                 255

Thr Arg His Lys Ala Trp Thr Leu Val Val Met Val Leu Ala Pro Tyr
            260                 265                 270
```

```
Thr Asn Asp Gln Thr Ile Gly Ser Thr Lys Ala Glu Val Tyr Val Asn
        275                 280                 285

Ile Ala Pro Thr Asn Val Tyr Val Ala Gly Glu Lys Pro Val Lys Gln
    290                 295                 300

Gly Ile Leu Pro Val Ala Val Ser Asp Gly Tyr Gly Gly Phe Gln Asn
305                 310                 315                 320

Thr Asp Pro Lys Thr Ser Asp Pro Val Tyr Gly His Val Tyr Asn Pro
                325                 330                 335

Ala Arg Thr Leu Tyr Pro Gly Arg Phe Thr Asn Leu Leu Asp Val Ala
            340                 345                 350

Glu Ala Cys Pro Thr Leu Leu Asp Phe Asn Gly Val Pro Tyr Val Gln
            355                 360                 365

Thr Gln Ser Asn Ser Gly Ser Lys Val Leu Ala Cys Phe Asp Leu Ala
    370                 375                 380

Phe Gly His Lys Asn Met Lys Asn Thr Tyr Met Ser Gly Leu Ala Gln
385                 390                 395                 400

Tyr Phe Ala Gln Tyr Ser Gly Thr Leu Asn Leu His Phe Met Tyr Thr
                405                 410                 415

Gly Pro Thr Asn Asn Lys Ala Lys Tyr Met Val Ala Tyr Ile Pro Pro
            420                 425                 430

Gly Thr His Pro Leu Pro Glu Thr Pro Glu Met Ala Ser His Cys Tyr
            435                 440                 445

His Ala Glu Trp Asp Thr Gly Leu Asn Ser Thr Phe Thr Phe Thr Val
    450                 455                 460

Pro Tyr Ile Ser Ala Ala Asp Tyr Ala Tyr Thr Ala Asp Glu Pro
465                 470                 475                 480

Glu Gln Ala Ser Val Gln Gly Trp Val Gly Val Tyr Gln Ile Thr Asp
                485                 490                 495

Thr His Glu Lys Asp Gly Ala Val Ile Val Thr Val Ser Ala Gly Pro
            500                 505                 510

Asp Phe Glu Phe Arg Met Pro Ile Ser Pro Ser Arg Gln Thr Thr Ser
            515                 520                 525

Ala Gly Glu Gly Ala Asp Pro Val Thr Thr Asp Ala Ser Ala His Gly
    530                 535                 540

Gly Asp Thr Arg Thr Thr Arg Arg Ala His Thr Asp Val Thr Phe Leu
545                 550                 555                 560

Leu Asp Arg Phe Thr Leu Val Gly Lys Thr Asn Asp Asn Lys Leu Val
                565                 570                 575

Leu Asp Leu Leu Ser Thr Lys Glu Lys Ser Leu Val Gly Ala Leu Leu
            580                 585                 590

Arg Ala Ala Thr Tyr Tyr Phe Ser Asp Leu Glu Val Ala Cys Val Gly
            595                 600                 605

Thr Asn Ala Trp Val Gly Trp Thr Pro Asn Gly Ser Pro Val Leu Thr
    610                 615                 620

Glu Val Gly Asp Asn Pro Val Val Phe Ser Arg Gly Thr Thr Arg
625                 630                 635                 640

Phe Ala Leu Pro Tyr Thr Ala Pro His Arg Val Leu Ala Thr Val Tyr
                645                 650                 655

Asn Gly Asp Cys Lys Tyr Lys Pro Thr Gly Thr Ala Pro Arg Glu Asn
            660                 665                 670

Ile Arg Gly Asp Leu Ala Thr Leu Ala Ala Arg Ile Ala Ser Glu Thr
            675                 680                 685
```

His Ile Pro Thr Thr Phe Asn Tyr Gly Met Ile Tyr Thr Gln Ala Glu
690                 695                 700

Val Asp Val Tyr Leu Arg Met Lys Arg Ala Glu Leu Tyr Cys Pro Arg
705                 710                 715                 720

Pro Val Leu Thr His Tyr Asp His Asn Gly Arg Asp Arg Tyr Lys Thr
            725                 730                 735

Thr Leu Val Lys Pro Ala Lys Gln
            740

<210> SEQ ID NO 10
<211> LENGTH: 740
<212> TYPE: PRT
<213> ORGANISM: Foot-and-mouth disease virus

<400> SEQUENCE: 10

Gly Ala Gly His Ser Ser Pro Val Thr Gly Ser Gln Asn Gln Ser Gly
1               5                   10                  15

Asn Thr Gly Ser Ile Ile Asn Asn Tyr Tyr Met Gln Gln Tyr Gln Asn
            20                  25                  30

Ser Met Asp Thr Gln Leu Gly Asp Asn Ala Ile Ser Gly Gly Ser Asn
        35                  40                  45

Glu Gly Ser Thr Asp Thr Thr Ser Thr His Thr Asn Asn Thr Gln Asn
50                  55                  60

Asn Asp Trp Phe Ser Lys Leu Ala Gln Ser Ala Ile Ser Gly Leu Phe
65                  70                  75                  80

Gly Ala Leu Leu Ala Asp Lys Lys Thr Glu Glu Thr Thr Leu Leu Glu
                85                  90                  95

Asp Arg Ile Val Thr Thr Arg His Gly Thr Thr Thr Ser Thr Thr Gln
            100                 105                 110

Ser Ser Val Gly Ile Thr Tyr Gly Tyr Ala Asp Ala Asp Ser Phe Arg
        115                 120                 125

Pro Gly Pro Asn Thr Ser Gly Leu Glu Thr Arg Val Glu Gln Ala Glu
130                 135                 140

Arg Phe Phe Lys Glu Lys Leu Phe Asp Trp Thr Ser Asp Lys Pro Phe
145                 150                 155                 160

Gly Thr Leu Tyr Val Leu Glu Leu Pro Lys Asp His Lys Gly Ile Tyr
                165                 170                 175

Gly Ser Leu Thr Asp Ala Tyr Tyr Met Arg Asn Gly Trp Asp Val
            180                 185                 190

Gln Val Ser Ala Thr Ser Thr Gln Phe Asn Gly Gly Ser Leu Leu Val
        195                 200                 205

Ala Met Val Pro Glu Leu Cys Ser Leu Lys Asp Arg Glu Glu Phe Gln
210                 215                 220

Leu Ser Leu Tyr Pro His Gln Phe Ile Asn Pro Arg Thr Asn Thr Thr
225                 230                 235                 240

Ala His Ile Gln Val Pro Tyr Leu Gly Val Asn Arg His Asp Gln Gly
                245                 250                 255

Lys Arg His Gln Ala Trp Ser Leu Val Val Met Val Leu Thr Pro Leu
            260                 265                 270

Thr Thr Glu Ala Gln Met Gln Ser Gly Thr Val Glu Val Tyr Ala Asn
        275                 280                 285

Ile Ala Pro Thr Asn Val Phe Val Ala Gly Glu Lys Pro Ala Lys Gln
290                 295                 300

Gly Ile Ile Pro Val Ala Cys Phe Asp Gly Tyr Gly Gly Phe Gln Asn
305                 310                 315                 320

```
Thr Asp Pro Lys Thr Ala Asp Pro Ile Tyr Gly Tyr Val Tyr Asn Pro
            325                 330                 335

Ser Arg Asn Asp Cys His Gly Arg Tyr Ser Asn Leu Leu Asp Val Ala
            340                 345                 350

Glu Ala Cys Pro Thr Phe Leu Asn Phe Asp Gly Lys Pro Tyr Val Val
            355                 360                 365

Thr Lys Asn Asn Gly Asp Lys Val Met Thr Cys Phe Asp Val Ala Phe
            370                 375                 380

Thr His Lys Val His Lys Asn Thr Phe Leu Ala Gly Leu Ala Asp Tyr
385                 390                 395                 400

Tyr Ala Gln Tyr Gln Gly Ser Leu Asn Tyr His Phe Met Tyr Thr Gly
            405                 410                 415

Pro Thr His His Lys Ala Lys Phe Met Val Ala Tyr Ile Pro Pro Gly
            420                 425                 430

Ile Glu Thr Asp Arg Leu Pro Lys Thr Pro Glu Asp Ala Ala His Cys
            435                 440                 445

Tyr His Ser Glu Trp Asp Thr Gly Leu Asn Ser Gln Phe Thr Phe Ala
            450                 455                 460

Val Pro Tyr Val Ser Ala Ser Asp Phe Ser Tyr Thr His Thr Asp Thr
465                 470                 475                 480

Pro Ala Met Ala Thr Thr Asn Gly Trp Val Ala Val Phe Gln Val Thr
            485                 490                 495

Asp Thr His Ser Ala Glu Ala Val Val Ser Val Ser Ala Gly
            500                 505                 510

Pro Asp Leu Glu Phe Arg Phe Pro Val Asp Pro Val Arg Gln Thr Thr
            515                 520                 525

Ser Ser Gly Glu Gly Ala Asp Val Val Thr Thr Asp Pro Ser Thr His
            530                 535                 540

Gly Gly Ala Val Thr Glu Lys Lys Arg Val His Thr Asp Val Ala Phe
545                 550                 555                 560

Val Met Asp Arg Phe Thr His Val Leu Thr Asn Arg Thr Ala Phe Ala
            565                 570                 575

Val Asp Leu Met Asp Thr Asn Glu Lys Thr Leu Val Gly Gly Leu Leu
            580                 585                 590

Arg Ala Ala Thr Tyr Tyr Phe Cys Asp Leu Glu Ile Ala Cys Leu Gly
            595                 600                 605

Glu His Glu Arg Val Trp Trp Gln Pro Asn Gly Ala Pro Arg Thr Thr
            610                 615                 620

Thr Leu Arg Asp Asn Pro Met Val Phe Ser His Asn Asn Val Thr Arg
625                 630                 635                 640

Phe Ala Val Pro Tyr Thr Ala Pro His Arg Leu Leu Ser Thr Arg Tyr
            645                 650                 655

Asn Gly Glu Cys Lys Tyr Thr Gln Gln Ser Thr Ala Ile Arg Gly Asp
            660                 665                 670

Arg Ala Val Leu Ala Ala Lys Tyr Ala Asn Thr Lys His Lys Leu Pro
            675                 680                 685

Ser Thr Phe Asn Phe Gly His Val Thr Ala Asp Lys Pro Val Asp Val
            690                 695                 700

Tyr Tyr Arg Met Lys Arg Ala Glu Leu Tyr Cys Pro Arg Pro Leu Leu
705                 710                 715                 720

Pro Gly Tyr Asp His Ala Asp Arg Asp Arg Phe Asp Ser Pro Ile Gly
            725                 730                 735
```

Val Glu Lys Gln
            740

<210> SEQ ID NO 11
<211> LENGTH: 740
<212> TYPE: PRT
<213> ORGANISM: Foot-and-mouth disease virus

<400> SEQUENCE: 11

Gly Ala Gly Gln Ser Ser Pro Ala Thr Gly Ser Gln Asn Gln Ser Gly
1               5                   10                  15

Asn Thr Gly Ser Ile Ile Asn Asn Tyr Tyr Met Gln Gln Tyr Gln Asn
            20                  25                  30

Ser Met Asp Thr Gln Leu Gly Asp Asn Ala Ile Ser Gly Gly Ser Asn
        35                  40                  45

Glu Gly Ser Thr Asp Thr Thr Ser Thr His Thr Asn Asn Thr Gln Asn
    50                  55                  60

Asn Asp Trp Phe Ser Lys Leu Ala Gln Ser Ala Ile Ser Gly Leu Phe
65                  70                  75                  80

Gly Ala Leu Leu Ala Asp Lys Lys Thr Glu Glu Thr Thr His Leu Glu
                85                  90                  95

Asp Arg Ile Leu Thr Thr Arg His Asn Thr Thr Thr Ser Thr Thr Gln
            100                 105                 110

Ser Ser Val Gly Val Thr Tyr Gly Tyr Ala Ser Ala Asp Arg Phe Leu
        115                 120                 125

Pro Gly Pro Asn Thr Ser Gly Leu Glu Ser Arg Val Glu Gln Ala Glu
    130                 135                 140

Arg Phe Phe Lys Glu Lys Leu Phe Thr Trp Thr Ala Ser Gln Glu Phe
145                 150                 155                 160

Ala His Val His Leu Leu Glu Leu Pro Thr Asp His Lys Gly Ile Tyr
                165                 170                 175

Gly Ala Met Val Glu Ser His Ala Tyr Val Arg Asn Gly Trp Asp Val
            180                 185                 190

Gln Val Ser Ala Thr Ser Thr Gln Phe Asn Gly Gly Thr Leu Leu Val
        195                 200                 205

Ala Met Val Pro Glu Leu His Ser Leu Asp Lys Arg Asp Val Ser Gln
    210                 215                 220

Leu Thr Leu Phe Pro His Gln Tyr Ile Asn Pro Arg Thr Asn Thr Thr
225                 230                 235                 240

Ala His Ile Val Val Pro Tyr Val Gly Val Asn Arg His Asp Gln Val
                245                 250                 255

Gln Met His Lys Ala Trp Thr Leu Val Val Ala Val Met Ala Pro Leu
            260                 265                 270

Thr Thr Ser Asn Met Gly Gln Asp Asn Val Glu Val Tyr Ala Asn Ile
        275                 280                 285

Ala Pro Thr Asn Val Tyr Val Ala Gly Glu Arg Pro Ser Lys Gln Gly
    290                 295                 300

Ile Ile Pro Val Ala Cys Asn Asp Gly Tyr Gly Gly Phe Gln Asn Thr
305                 310                 315                 320

Asp Pro Lys Thr Ala Asp Pro Ile Tyr Gly Leu Val Ser Asn Ala Pro
                325                 330                 335

Arg Thr Ala Phe Pro Gly Arg Phe Thr Asn Leu Leu Asp Val Ala Glu
            340                 345                 350

Ala Cys Pro Thr Phe Leu Asp Phe Asp Gly Thr Pro Tyr Val Lys Thr
        355                 360                 365

```
Arg His Asn Ser Gly Ser Lys Ile Leu Ala His Ile Asp Leu Ala Phe
    370                 375                 380

Gly His Lys Ser Phe Lys Asn Thr Tyr Leu Ala Gly Leu Ala Gln Tyr
385                 390                 395                 400

Tyr Ala Gln Tyr Ser Gly Ser Ile Asn Leu His Phe Met Tyr Thr Gly
                405                 410                 415

Pro Thr Gln Ser Lys Ala Arg Phe Met Val Ala Tyr Ile Pro Pro Gly
                420                 425                 430

Thr Ser Pro Val Pro Asp Thr Pro Glu Lys Ala Ala His Cys Tyr His
        435                 440                 445

Ser Glu Trp Asp Thr Gly Leu Asn Ser Lys Phe Thr Phe Thr Val Pro
    450                 455                 460

Tyr Met Ser Ala Ala Asp Phe Ala Tyr Thr Tyr Cys Asp Glu Pro Glu
465                 470                 475                 480

Gln Ala Ser Ala Gln Gly Trp Val Thr Leu Tyr Gln Ile Thr Asp Thr
                485                 490                 495

His Asp Pro Asp Ser Ala Val Leu Val Ser Val Ser Ala Gly Ala Asp
                500                 505                 510

Phe Glu Leu Arg Leu Pro Ile Asn Pro Ala Thr Gln Thr Thr Ser Ala
        515                 520                 525

Gly Glu Gly Ala Asp Val Val Thr Thr Asp Val Thr Thr His Gly Gly
    530                 535                 540

Glu Val Ser Val Pro Arg Arg Gln His Thr Asn Val Glu Phe Leu Leu
545                 550                 555                 560

Asp Arg Phe Thr His Val Gly Lys Val Asn Glu Ser Arg Thr Ile Ser
                565                 570                 575

Leu Met Asp Thr Lys Glu His Thr Leu Val Gly Ala Ile Leu Arg Ser
                580                 585                 590

Ala Thr Tyr Tyr Phe Cys Asp Leu Glu Val Ala Ile Leu Gly Thr Ala
        595                 600                 605

Pro Trp Ala Ala Trp Val Pro Asn Gly Cys Pro His Thr Gly Arg Val
    610                 615                 620

Glu Asp Asn Pro Val Val His Ser Lys Gly Ser Val Val Arg Phe Ala
625                 630                 635                 640

Leu Pro Tyr Thr Ala Pro His Gly Val Leu Ala Thr Val Tyr Asn Gly
                645                 650                 655

Asn Cys Lys Tyr Ser Glu Thr Gln Arg Val Thr Ser Arg Arg Gly Asp
                660                 665                 670

Leu Ala Val Leu Ala Gln Arg Val Glu Asn Glu Thr Thr Arg Cys Leu
        675                 680                 685

Pro Thr Thr Phe Asn Phe Gly Arg Leu Leu Cys Glu Glu Gly Asp Ala
    690                 695                 700

Tyr Tyr Arg Met Lys Arg Ala Glu Leu Tyr Cys Pro Arg Pro Leu Arg
705                 710                 715                 720

Val Arg Tyr Thr His Thr Thr Asp Arg Tyr Lys Thr Pro Leu Val Lys
                725                 730                 735

Pro Asp Lys Gln
            740
```